US008530673B2

(12) United States Patent
Shinoda et al.

(10) Patent No.: US 8,530,673 B2
(45) Date of Patent: *Sep. 10, 2013

(54) TETRATHIAFULVALENE DERIVATIVE, AND ORGANIC FILM AND ORGANIC TRANSISTOR USING THE SAME

(75) Inventors: Masato Shinoda, Kanagawa (JP); Satoshi Yamamoto, Kanagawa (JP); Toshiya Sagisaka, Kanagawa (JP); Takuji Kato, Fukuoka (JP); Takashi Okada, Kanagawa (JP); Daisuke Goto, Kanagawa (JP); Shinji Matsumoto, Kanagawa (JP); Masataka Mohri, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/259,535

(22) PCT Filed: Mar. 17, 2010

(86) PCT No.: PCT/JP2010/055143
§ 371 (c)(1),
(2), (4) Date: Sep. 23, 2011

(87) PCT Pub. No.: WO2010/110351
PCT Pub. Date: Sep. 30, 2010

(65) Prior Publication Data
US 2012/0035364 A1   Feb. 9, 2012

(30) Foreign Application Priority Data

Mar. 25, 2009 (JP) .................................. 2009-073990
Jan. 5, 2010 (JP) .................................. 2010-000319

(51) Int. Cl.
C07D 339/06   (2006.01)
C07D 241/36   (2006.01)
H01L 29/00   (2006.01)

(52) U.S. Cl.
USPC ............... 549/31; 549/29; 544/336; 544/343; 257/40

(58) Field of Classification Search
USPC ................ 549/29, 31; 544/336, 343; 257/40
See application file for complete search history.

(56) References Cited

FOREIGN PATENT DOCUMENTS

JP      2007 042717      2/2007

OTHER PUBLICATIONS

Papavassiliou, G. C., et al., "Bis(pyrazino)tetrathiafulvalene and Similar C-K40 Donors," Chemica Scripta, vol. 27, No. 2, pp. 265-268, (1987).
Naraso, et al., "High Performance n- and p-Type Field-Effect Transistors Based on Tetrathiafulvalene Derivatives," Journal of the American Chemical Society, vol. 128, No. 30, pp. 9598-9599, (Jul. 7, 2006).
Naraso, et al., "High-Performance Organic Field-Effect Transistors Based on C-K40-Extended Tetrathiafulvalene Derivatives," Journal of the American Chemical Society, vol. 127, No. 29, pp. 10142-10143, (Jun. 29, 2005).
Mas-Torrent, M., et al., "High Mobility of Dithiophene-Tetrathiafulvalene Single-Crystal Organic Field Effect Transistors," Journal of the American Chemical Society, vol. 126, No. 4, pp. 984-984, (2004).
Mas-Torrent, M., et al., "Single-crystal organic field-effect transistors based on dibenzo-tetrathiafulvalene," Applied Physics Letters, vol. 86, Total 3 Pages, (2005).
International Search Report Issued Jul. 13, 2010 in PCT/JP10/055143 Filed Mar. 17, 2010.

*Primary Examiner* — Golam M M Shameem
(74) *Attorney, Agent, or Firm* — Oblon, Spivak, McClelland, Maier & Neustadt, L.L.P.

(57) ABSTRACT

A tetrathiafulvalene derivative expressed by General Formula (I): General Formula (I) in General Formula (I), X represents an atom selected from a carbon atom, a sulfur atom, and a nitrogen atom, and Xs may be the same or different; provided that when X is the carbon atom or the nitrogen atom, $R_1$ to $R_8$ each represent one of a hydrogen atom, a halogen atom, a substituted or unsubstituted alkyl group, a substituted or unsubstituted alkoxy group, and a substituted or unsubstituted thioalkoxy group, and may be the same or different; and $Y_1$ and $Y_2$ each represent one of structures expressed by General Formulas (II) and (III), and may be the same or different: General Formula (II) General Formula (III).

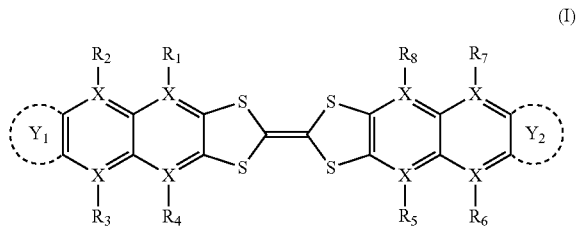

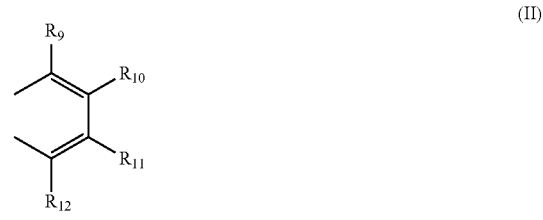

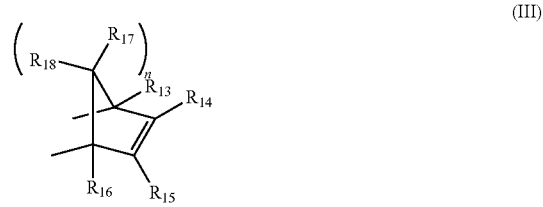

7 Claims, 8 Drawing Sheets

TETRATHIAFULVALENE DERIVATIVE, AND ORGANIC FILM AND ORGANIC TRANSISTOR USING THE SAME

TECHNICAL FIELD

The present invention relates to a novel tetrathiafulvalene derivative, and an organic electronic device using the novel tetrathiafulvalene derivative, for example, an organic TFT, an electrochromic display, an EL display, an organic semiconductor material, and a raw material for charge transport material.

BACKGROUND ART

Tetrathiafulvalene (TTF) and its derivatives are molecules having strong electron donating properties, and form a charge-transfer complex together with an electron acceptor molecule such as tetracyanoquinodimethane (TCNQ). The resultant charge-transfer complex exhibits a metallic conductivity. The charge-transfer complex is expected to use in many applications, such as organic superconductors, organic magnetic materials, organic electrochromic materials and organic electroluminescence materials.

In recent years, thin-film transistors using organic semiconductors have attracted attention. Conventional processes for producing a thin-film transistor using silicon need vacuum conditions and a depositing step. Therefore, the conventional processes for producing a thin-film transistor have a disadvantage of requiring a very expensive production facility. However, a process for producing a transistor using the organic semiconductor can be reduced in cost, because of on-demand production of the transistor by a printing process using an ink formed by dissolving an organic semiconductor material in a solvent. Moreover, by means of the printing process using the organic semiconductor, an electronic circuit can be enlarged in area, or a flexible device can be produced.

It has been confirmed that a thin-film transistor using a TTF derivative, which has been conventionally reported, has a high field-effect mobility among organic semiconductors. In Non-Patent Literatures 1 and 2, by dissolving a TTF derivative in a solvent, a crystal is produced, and the crystal is placed between a source electrode and a drain electrode, so as to produce an organic semiconductor layer, and then transistor characteristics thereof is measured. It is confirmed that a thin-film transistor using DB-TTF as the organic semiconductor layer has a high mobility. However, a process for producing an element by placing a single crystal on the organic semiconductor layer of the thin-film transistor, is not practically employed as a process in which industrial convenience is considered. Additionally, typical TTF derivatives have a low ionization potential and poor atmospheric stability.

Non-Patent Literature 3 and Patent Literature 1 propose a molecular structure containing a nitrogen atom in order to improve an ionization potential of DB-TTF and DN-TTF. The DB-TTF and DN-TTF each containing a nitrogen atom is improved in ionization potential, but significantly decreased in mobility, by comparison with DB-TTF and DN-TTF, in which a nitrogen atom has not been contained.

CITATION LIST

Patent Literature

PTL 1: Japanese Patent Application Laid-Open (JP-A) No. 2007-42717

Non-Patent Literature

NPL 1: J. Am. Chem. Soc. 2004, 126, 984-985
NPL 2: Appl. Phys. Lett. 2005, 86 012110
NPL 3: J. Am. Chem. Soc. 2005, 127, 10142-10143

SUMMARY OF INVENTION

In view of the current situation of the conventional technologies, an object of the present invention is to provide a tetrathiafulvalene derivative having a specific structure, which maintains high mobility, and has deeper ionization potential than that of a conventional tetrathiafulvalene derivative, and to provide an organic film, and an organic transistor using the tetrathiafulvalene derivative having a specific structure.

The inventors of the present invention have been intensively studied to achieve the object of the present invention, and found that it is effective to use the trathiafulvalene derivative having a specific structure in an organic electronic device.

The present invention is achieved as follows.

<1> A tetrathiafulvalene derivative expressed by General Formula (I);

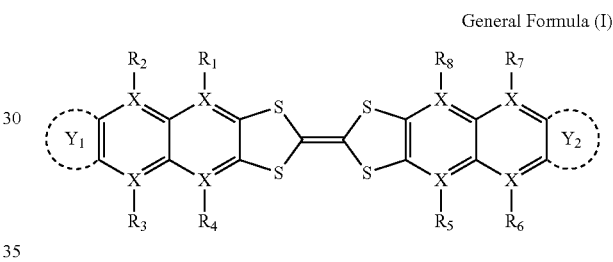

General Formula (I)

in General Formula (I), X represents an atom selected from a carbon atom, a sulfur atom, and a nitrogen atom, and Xs may be the same or different; provided that when X is the carbon atom or the nitrogen atom, $R_1$ to $R_8$ each represent one of a hydrogen atom, a halogen atom, a substituted or unsubstituted alkyl group, a substituted or unsubstituted alkoxy group, and a substituted or unsubstituted thioalkoxy group, and may be the same or different; and $Y_1$ and $Y_2$ each represent one of structures expressed by General Formulas (II) and (III), and may be the same or different:

General Formula (II)

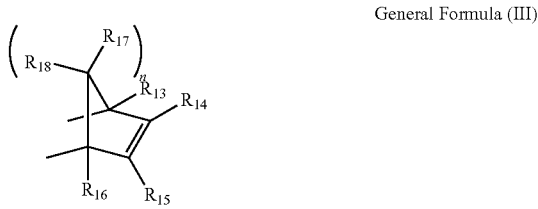

General Formula (III)

in General Formulas (II) and (III), $R_9$ to $R_{18}$ each represent one of a hydrogen atom, a halogen atom, a substituted or unsubstituted alkyl group, a substituted or unsubstituted alkoxy group, and a substituted or unsubstituted thioalkoxy group, and may be the same or different; n represents an integer of 1 to 3; and provided that when n is an integer of 2 or 3, $R_{17}$s may be the same or different and $R_{18}$s may be the same or different.

<2> An organic film including the tetrathiafulvalene derivative according to <1>.

<3> An organic transistor including the tetrathiafulvalene derivative according to <1>.

According to the present invention, a tetrathiafulvalene derivative useful for an organic electronic device, and an organic film and an organic transistor using the tetrathiafulvalene derivative.

DESCRIPTION OF EMBODIMENTS

Figure 1A:
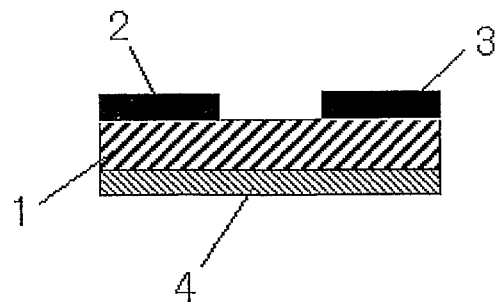
FIGS. 1A to 1D schematically show organic thin-film transistors of the present invention.
Figure 1B:
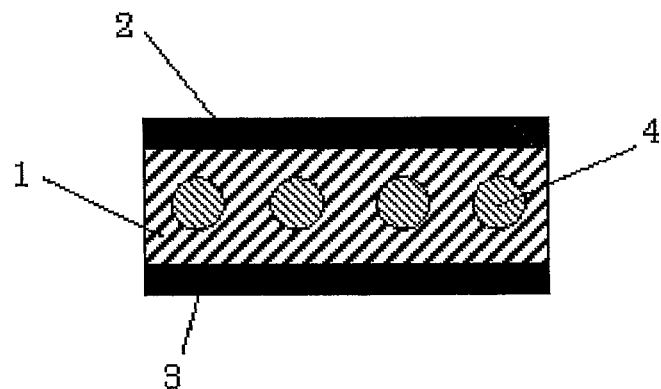
Figure 1C:
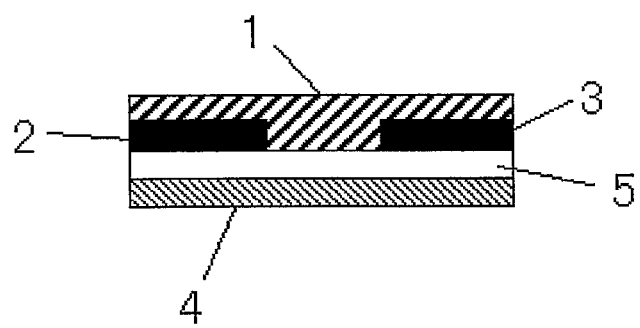

A feature of the present invention is a tetrathiafulvalene derivative expressed by General Formula (I).

Tetrathiafulvalene has such a structure that a heterocyclic part has 7 π electrons, from which one electron tends to be released so that the heterocyclic part has 6 π electrons, which satisfies Hückel's rule. That is, the tetrathiafulvalene structure exhibits excellent electron donating properties. By virtue of the donating properties, tetrathiafulvalene is likely to be a radical cation, and is stable in the radical cation state. Thus, it is preferably used as a p-type semiconductor material. However, tetrathiafulvalene has low ionization potential, and poor resistance to oxygen due to the donating properties. The material expressed by General Formula (I) has a molecular structure, in which a conjugated system in a molecule is extended, compared to the conventional tetrathiafulvalene derivatives. It is suggested that the donating properties of tetrathiafulvalene may be lowered by extending the conjugated system. Namely, the ionization potential of the tetrathiafulvalene derivative expressed by General Formula (I) increases, thereby exhibiting excellent resistant to oxygen causing degradation. Therefore, the tetrathiafulvalene derivative expressed by General Formula (I) is more stable than that of the conventional tetrathiafulvalene derivative. Moreover, the extension of the conjugated system in the molecule enlarges an area of electron transfer path, so that excellent electron and hole transport is expected.

Specific examples of the novel tetrathiafulvalene derivative of the present invention will be described below.

Examples of $R_1$ to $R_8$ in General Formula (I) include a hydrogen atom, halogen atom, a substituted or unsubstituted alkyl group, a substituted or unsubstituted alkoxy group and a substituted or unsubstituted thioalkoxy group, and $R_1$ to $R_8$ may the same or different.

As the substituted or unsubstituted alkyl group, a straight, branched or cyclic alkyl group having 1 or more carbon atoms is used. Moreover, the alkyl group may have a phenyl group which is substituted with a halogen atom (for example, a fluorine atom, a chlorine atom, a bromine atom, an iodine atom), a cyano group, a phenyl group, or a straight and/or branched alkyl group.

Specific examples of the substituted or unsubstituted alkyl group include a methyl group, ethyl group, n-propyl group, i-propyl group, t-butyl group, s-butyl group, n-butyl group, i-butyl group, pentyl group, hexyl group, heptyl group, octyl group, nonyl group, decyl group, undecyl group, dodecyl group, tridecyl group, tetradecyl group, pentadecane group, hexadecyl group, heptadecyl group, octadecyl group, 3,7-dimethyloctyl group, 2-ethylhexyl group, trifluoromethyl group, trifluorooctyl group, trifluorododecyl group, trifluorooctadecyl group, 2-cyanoethyl group, benzyl group, 4-chlorobenzyl group, 4-methylbenzyl group, cyclopentyl group and cyclohexyl group.

Specific examples of the substituted or unsubstituted alkoxy group or the substituted or unsubstituted thioalkoxy group include those formed by introducing an oxygen atom or a sulfur atom to the binding position of each of the above-exemplified alkyl groups.

Moreover, specific examples of the tetrathiafulvalene derivatives of the present invention will be listed below.

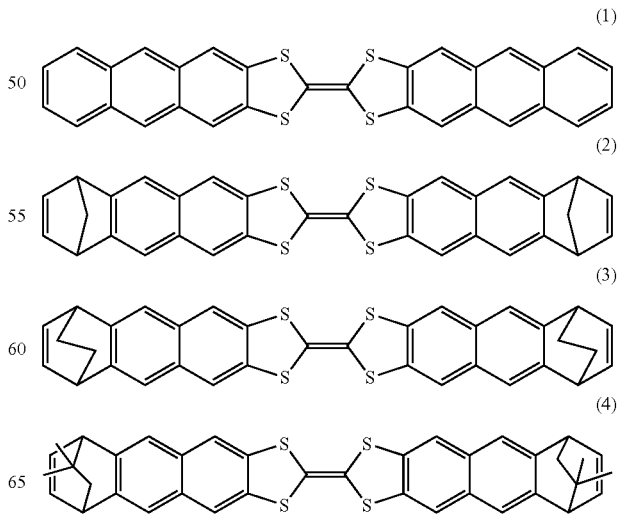

(5)
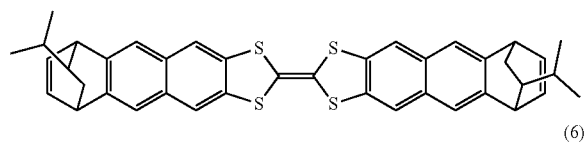
(6)
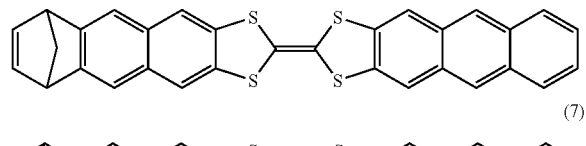
(7)
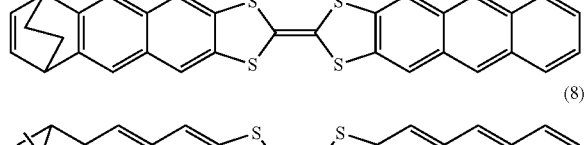
(8)
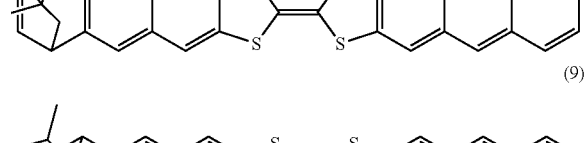
(9)
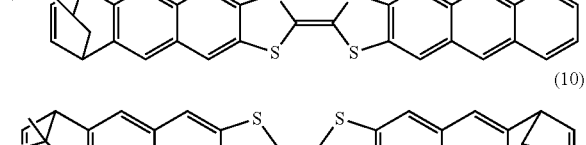
(10)
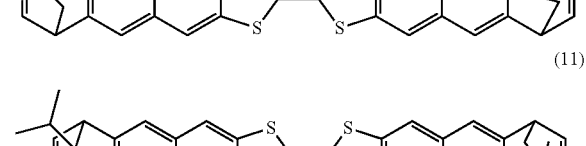
(11)
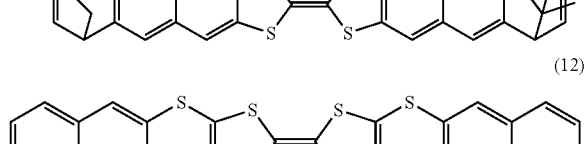
(12)
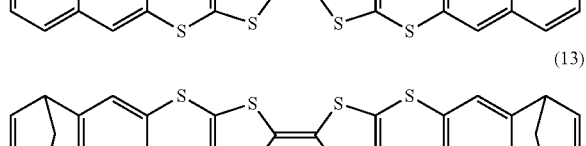
(13)
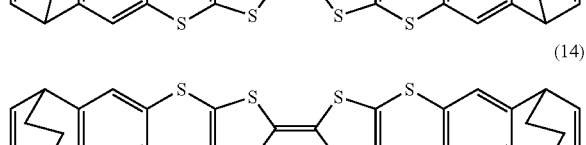
(14)
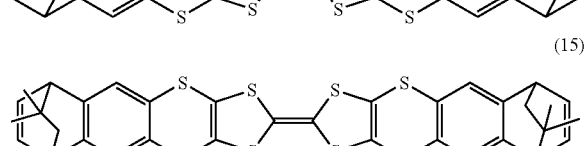
(15)
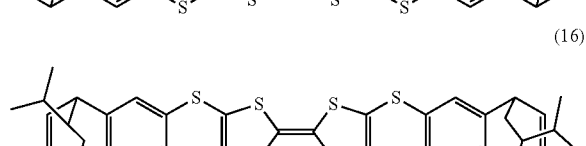
(16)
(17)
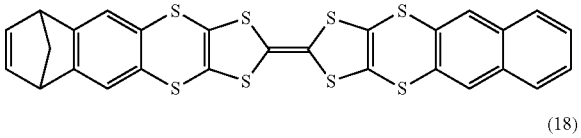
(18)
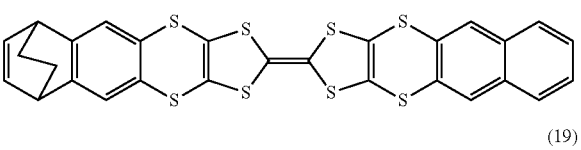
(19)
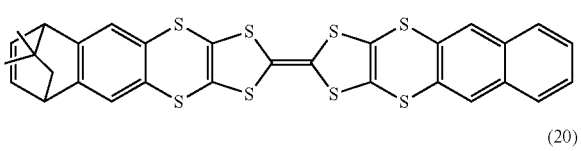
(20)
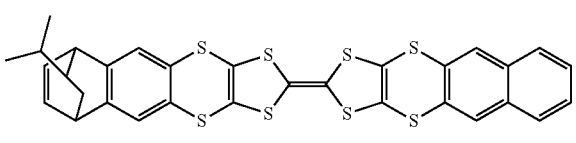
(21)
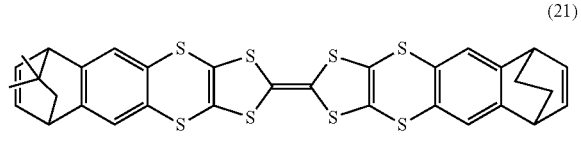
(22)
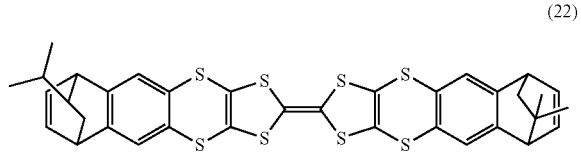
(23)
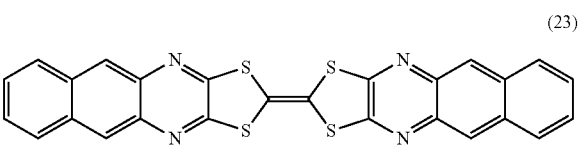
(24)
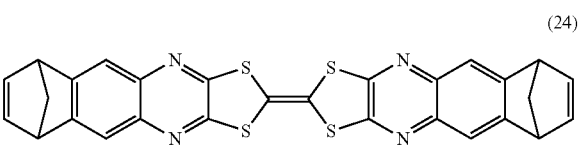
(25)
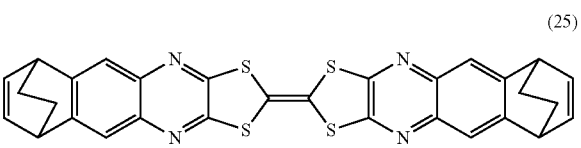
(26)
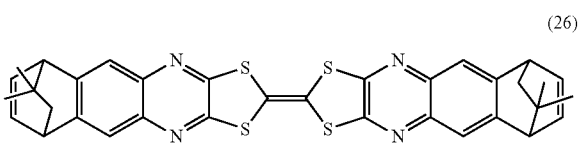
(27)
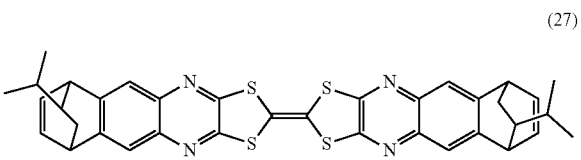

 (28)
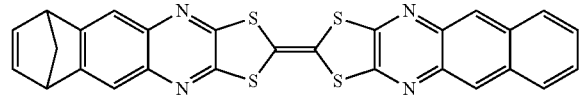 (29)
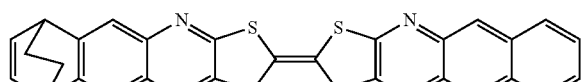 (30)
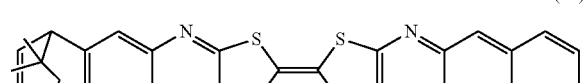 (31)
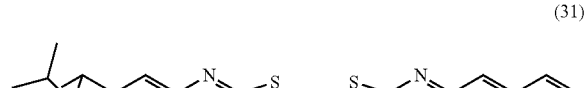 (32)
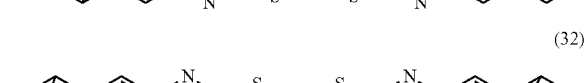 (33)
 (34)
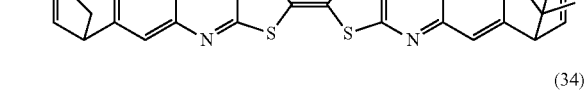 (35)
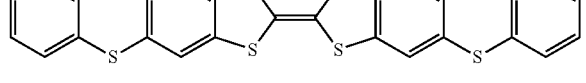 (36)
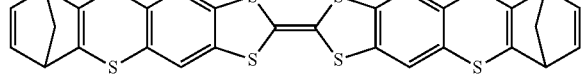 (37)
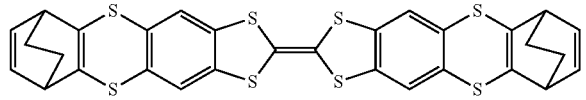 (38)
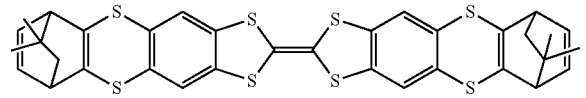 (39)
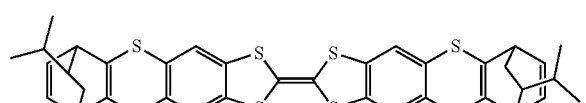 (40)
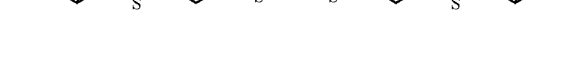 (41)
 (42)
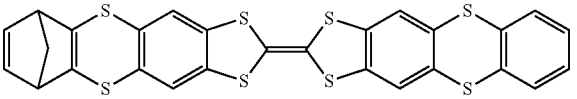 (43)
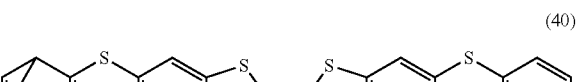 (44)
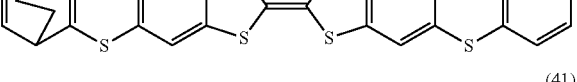 (45)
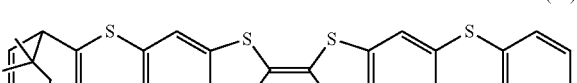 (46)
 (47)
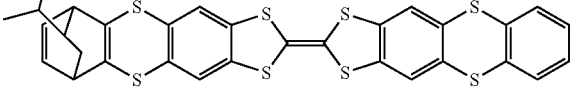 (48)
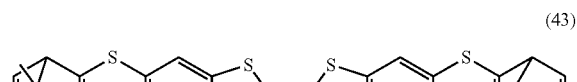 (49)
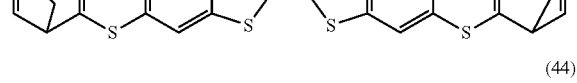
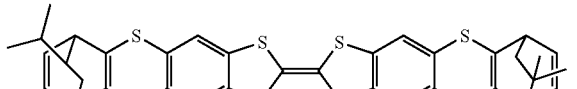
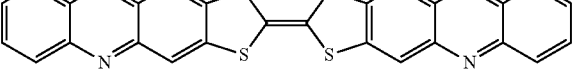
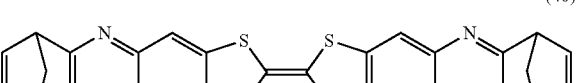

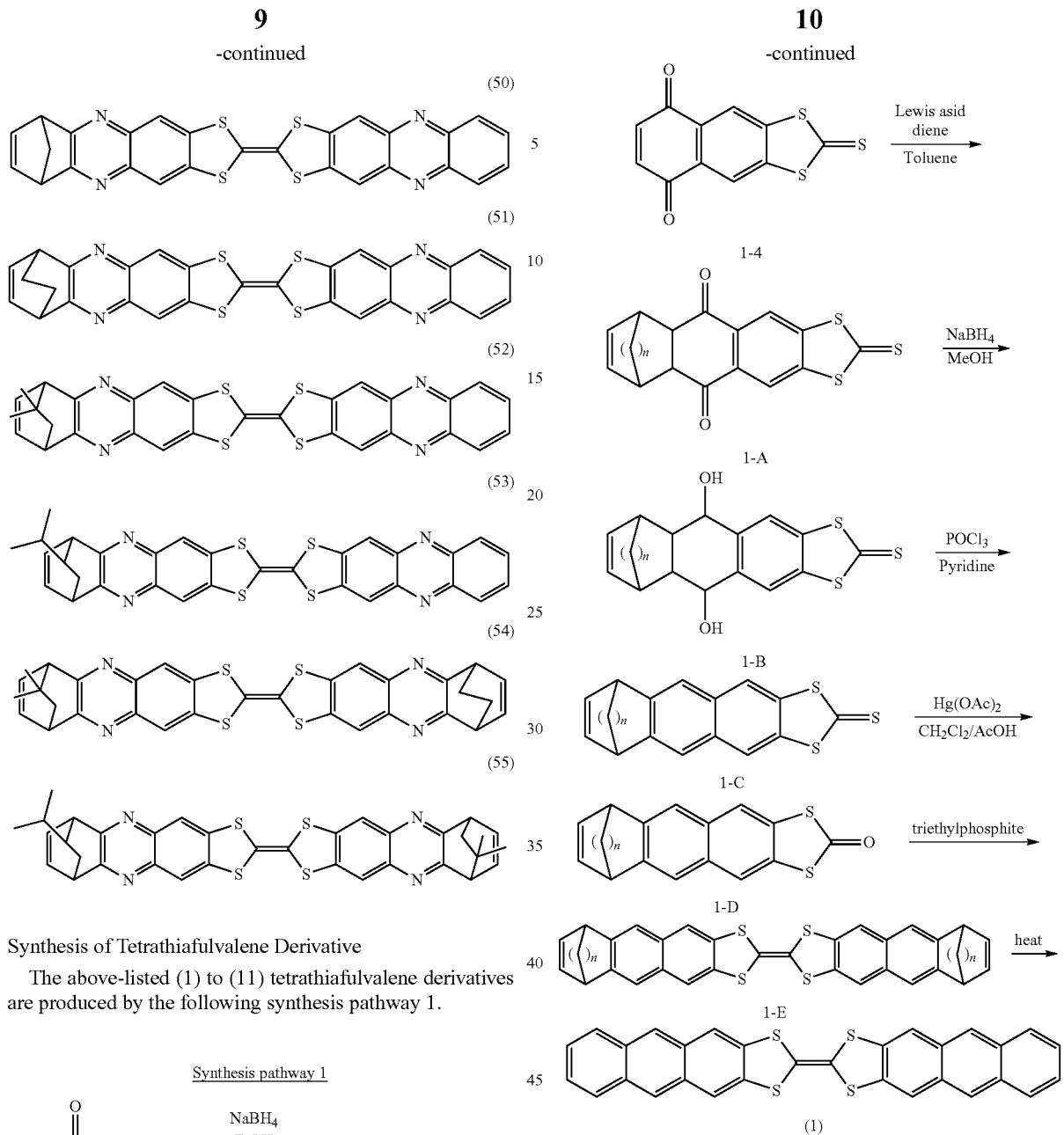

Synthesis of Tetrathiafulvalene Derivative

The above-listed (1) to (11) tetrathiafulvalene derivatives are produced by the following synthesis pathway 1.

"DDQ" described in the third step is an abbreviation of 2,3-dichloro-5,6-dicyano-1,4-benzoquinone.

The reaction from the first step to the third step is performed referring to the methods described in J. Org. Chem. 1994, 59, 6519-6527, Chem. Commun. 1998, 361-362, Chem. Commun. 1998, 2197-2198, Tetrahedron Letters 2000, 41, 2091-2095.

Compound (1-A) synthesized in the reaction of the fourth step is obtained by the Diels-Alder reaction between dienophile (1-4) and a diene corresponding to the molecular structure expressed by General Formula (III). In the Diels-Alder reaction, the reactivity depends on the energy difference between LUMO of the dienophile and HOMO of the diene. The smaller the energy difference is, the higher the reactivity is. The larger the energy difference is, the lower the reactivity is. When the energy difference between LUMO of the dienophile and HOMO of the diene is large, a Lewis acid is preferably added as a catalyst in order to improve the reactivity.

The Lewis acid coordinates to the carbonyl oxygen of dienophile (1-4), lowering its LUMO energy to accelerate the Diels-Alder reaction.

Examples of the Lewis acid used in the above reaction include borontrifluoride, aluminum chloride, ferric chloride, stannous chloride, stannic chloride, titanic chloride, zinc chloride, and N-(trimethylsilyl)bis(trifluoromethanesulfonyl)imide.

The reaction of the fifth step is to reduce (convert) the carbonyl compound to an alcohol compound using a metal hydride.

Examples of reducing agents include sodium borohydride, lithium aluminium hydride, diisobutylaluminium hydride, sodium cyanoborohydride, lithium borohydride, lithium triethylborohydride, borane complex, triethylsilane, sodium bis(2-methoxyethoxy)alminium hydride, nickel borohydride, sodium tri(acetoxy)borohydride, zinc borohydride, and lithium tri(sec-butyl)borohydride.

In the reaction of the sixth step, compound (1-C) is obtained by intramolecular dehydration.

In the reactions of the seventh and eighth steps, compound (1-E) is produced by a coupling reaction via thione compound (1-D), as described in J. Org. Chem., 2000, 65, 5794-5805.

The tetrathiafulvalene derivative having a molecular structure expressed by General Formula (II) can be produced by heating compound (1-E) in the ninth step so as to cause a reverse Diels-Alder reaction.

The above-listed (12) to (22) tetrathiafulvalene derivatives can be produced by the following synthesis pathway 2.

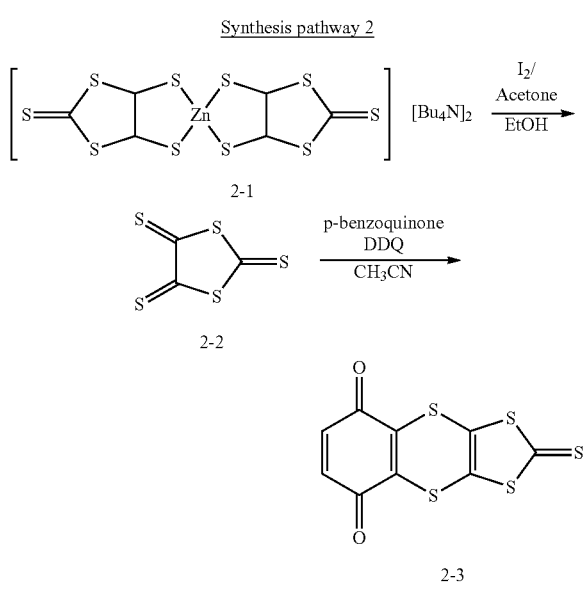

As shown in synthesis pathway 2, using bis(tetra-n-butyl ammonium)bis(1,3-dithiole-2-thione-4,5-dithiolato)zinc complex (2-1) as a starting material, compound (2-2) is produced referring to the literature SYNTHSIS 1995, 215-235. p-Benzoquinone is cycloadded to compound (2-2) by the Diels-Alder reaction, followed by dehydration with DDQ, to thereby obtain compound (2-3). Then, compound (2-3) is treated following the same reaction scheme starting from compound (1-4) in synthesis pathway 1, whereby (12) to (22) tetrathiafulvalene derivatives are synthesized.

The above-listed (23) to (33) tetrathiafulvalene derivatives can be produced by the following synthesis pathway 3.

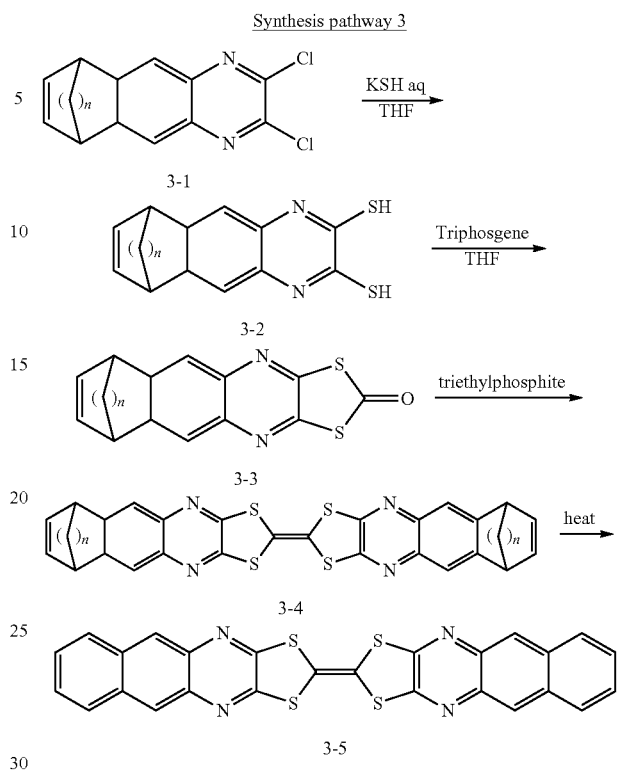

"THF" is an abbreviation of tetrahydrofran.

As shown in synthesis pathway 3, dichloro compound (3-1) is converted to dithiol compound (3-2) using a potassium hydrosulfide solution, and then formed into a thione compound using triphosgene. Then, thione compound (3-3) is treated following the same reaction scheme starting from compound (1-D) in synthesis pathway 1, whereby (23) to (33) tetrathiafulvalene derivatives are synthesized.

The above-listed (34) to (55) tetrathiafulvalene derivatives can be produced by the following synthesis pathway 4.

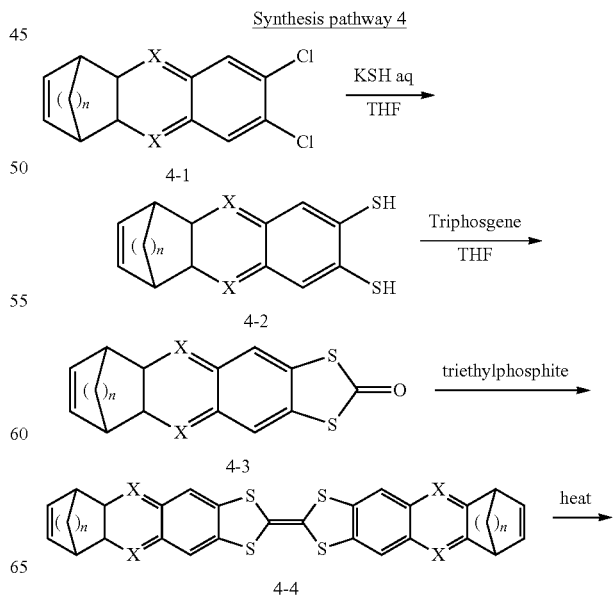

-continued

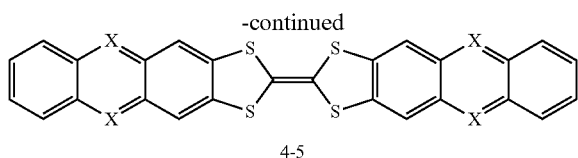

4-5

In synthesis pathway 4, X represents a sulfur atom or a nitrogen atom.

The (34) to (55) tetrathiafulvalene derivatives are obtained from dichloro compound (4-1) following the same pathway as synthesis pathway 3.

Transistor Configuration

FIGS. 1A to 1D show schematic configurations of organic thin-film transistors according to the present invention. An organic semiconductor layer 1 of the organic thin-film transistor of the present invention mainly contains the tetrathiafulvalene derivative expressed by General Formula (I). The organic thin-film transistor of the present invention includes a source electrode 2, a drain electrode 3 and a gate electrode 4, which are provided on the organic semiconductor layer 1 with being separated each other. A gate insulating film 5 may be provided between the gate electrode 4 and the organic semiconductor layer 1. The organic thin-film transistor is configured to control the current flowing through the organic semiconductor layer 1 between the source electrode 2 and the drain electrode 3 by applying voltage to the gate electrode 4. The organic thin-film transistor of the present invention may be formed on a substrate. As the substrate, a typical substrate formed of, for example, glass, silicon, plastic or the like may be used. A conductive substrate can be used to serve as the gate electrode. The gate electrode and the conductive substrate may be layered. However, a plastic sheet is preferably used as the substrate in the case where a device, to which the organic thin-film transistor of the present invention is applied, is expected to have properties such as flexibility, lightweight, lower production cost and shock resistance.

Examples of the plastic sheets include films of polyethylene terephthalate, polyethylene naphthalate, polyether sulfone, polyetherimide, polyether ether ketone, polyphenylene sulfide, polyarylate, polyimide, polycarbonate, cellulose triacetate, and cellulose acetate propionate.

Organic Semiconductor Layer

Organic semiconductor materials used in the present invention can be film deposited by vapor phase. The organic semiconductor material is heated in vacuum, so as to be vapor deposited on a desired area, to thereby form a thin film. Additionally, the organic semiconductor material is dissolved in a solvent such as dichloromethane, tetrahydrofuran, chloroform, toluene, dichlorobenzene and/or xylene, and applied on a substrate so as to deposit a thin film.

Examples of methods for depositing the organic semiconductor thin film include spray coating, spin coating, blade coating, dipping, casting, roll coating, bar coating, dye coating, inkjetting and dispensing. From the above-described deposition methods and solvents, a deposition method and solvent may be appropriately selected according to materials.

In the organic thin-film transistor of the present invention, the thickness of the organic semiconductor layer is not particularly limited, and the thickness of the organic semiconductor layer is so selected as to deposit a uniform thin film, namely, a thin film having no gaps and holes that adversely affect the carrier transportation characteristics of the organic semiconductor layer.

The thickness of the organic semiconductor layer is generally 1 μm or less, and particularly preferably 5 nm to 200 nm.

In the organic thin-film transistor of the present invention, the organic semiconductor layer mainly formed of the tetrathiafulvalene derivative is formed in contact with the source electrode, the drain electrode, and the insulating film.

Insulating Film

The insulating film used in the organic thin-film transistor of the present invention is formed of various materials for insulating film. Examples thereof include inorganic insulating materials such as silicon oxide, silicon nitride, aluminum oxide, aluminum nitride, titanium oxide, tantalum oxide, tin oxide, vanadium oxide, barium-strontium-titanium oxide, barium-titanium-zirconium oxide, lead-zirconium-titanium oxide, lead lanthanum titanate, strontium titanate, barium titanate, barium magnesium fluoride, bismuth-niobium-tantalum oxide and yttrium trioxide.

Additionally, examples thereof include polymer compounds such as polyimides, polyvinyl alcohols, polyvinyl phenols, polyesters, polyethylene, polyphenylenesulfides, unsubstituted or halogen atom substituted polyp araxylylene, polyacrylonitrile and cyanoethylpullulan.

These insulating materials may be used in combination. The insulating material is not particularly limited, and it is preferred to select an insulating material having a high dielectric constant and a low conductivity.

Examples of the methods of depositing the insulating film using the insulating materials include dry deposition processes such as a chemical vacuum deposition (CVD), a plasma CVD and a plasma polymerization; and wet coating processes such as spray coating, spin coating, dip coating, inkjetting, casting, blade coating and bar coating. Modification of Interface between Organic Semiconductor and Insulating Film such as HMDS.

In the organic thin-film transistor of the present invention, the organic thin film may be provided between the insulating film and the organic semiconductor layer to improve adhesiveness thereof, decrease gate voltage and reduce leak current. The organic thin film is not particularly limited as long as the organic thin film does not have a chemical effect on an organic semiconductor layer. For example, an organic molecular film and a polymer thin film can be used.

As the organic molecular film, coupling agents such as octadecyl trichlorosilane (ODTCS), and hexamethylene disilazane (HMDS) may be used. In addition, as the polymer thin film, the aforementioned polymer insulating materials can be used, and these may function as a sort of the insulating film. This organic thin film may be subject to an anisotropic treatment by rubbing or the like.

Electrode

The materials of the gate electrode and the source electrode used in the organic thin-film transistor of the present invention are not particularly limited, as long as conductive materials are used. Examples thereof include platinum, gold, silver, nickel, chromium, copper, iron, tin, antimony, lead, tantalum, indium, aluminum, zinc, magnesium, and alloys thereof conductive metal oxides such as indium/tin oxides; organic and inorganic semiconductors in which conductivity is improved by doping, etc., such as a silicon single crystal, polysilicon, amorphous silicon, germanium, graphite, polyacetylene, polyparaphenylene, polythiophene, polypyrrol, polyaniline, polythienylene vinylene, polyparaphenylene vinylene, complexes consisting of polyethylene dioxythiophene and polystyrene sulfonic acid.

Of the conductive materials described above, materials having a low electric resistance at the surface in contact with the semiconductor layer are preferred for the source electrode and drain electrode. Moreover, when the tetrathiafulvalene derivative of the present invention is used in the semiconductor layer, by forming an electrode, which becomes an electrical contact point, using a charge-transfer complex consisting of the tetrathiafulvalene derivative and an electron acceptor molecule such as tetracyanoquinodimethane (TCNQ), carriers can be effectively injected.

Examples of methods for forming an electrode include a method in which a conductive thin film, which has been deposited using the material mentioned above by deposition or sputtering, is formed into an electrode by a known method such as a photolithographic method or liftoff technology; and a method in which an electrode is formed by etching a resist on a metal foil of, for example, aluminum and copper, by thermal transfer, inkjet or the like. In addition, an electrode may be formed by directly patterning by inkjet printing using a solution or dispersion liquid of a conductive polymer or a dispersion liquid of conductive particles, or may be formed from a coated layer by lithography or laser ablation. It is also possible to use a method in which an ink, conductive paste, etc. containing conductive polymers or conductive particles are patterned by a printing method such as relief printing, intaglio printing, planographic printing or screen printing.

Extraction Electrode, Protective Layer

The organic thin-film transistor of the present invention can be provided with an extraction electrode from each electrode, as necessary.

The organic thin-film transistor of the present invention can be provided with a protective layer in terms of protection from moisture, atmosphere and/or gas, and protection for integration of a device for convenience.

Applied Device

The organic thin-film transistors of the present invention can be utilized as an element for driving image display elements such as liquid crystal, organic electroluminescence, and electrophoretic migration. When such elements are integrated, it is possible to produce a display referred to as "electronic paper". Moreover, it is also possible to use an IC in which the organic thin-film transistors of the present invention are integrated as a device such as an IC tag.

EXAMPLES

Hereinafter, the present invention will be specifically explained with reference to Examples. However, it should be noted that the present invention is not confined to these Examples in any way.

Example 1

Synthesis of bis(6,9-dihydro-6,9-ethanoanthra[2,3-d])tetrathiafulvalene: tetrathiafulvalene derivative (3)

A synthesis route of compound (3) is as follows.

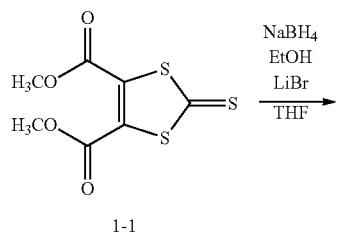

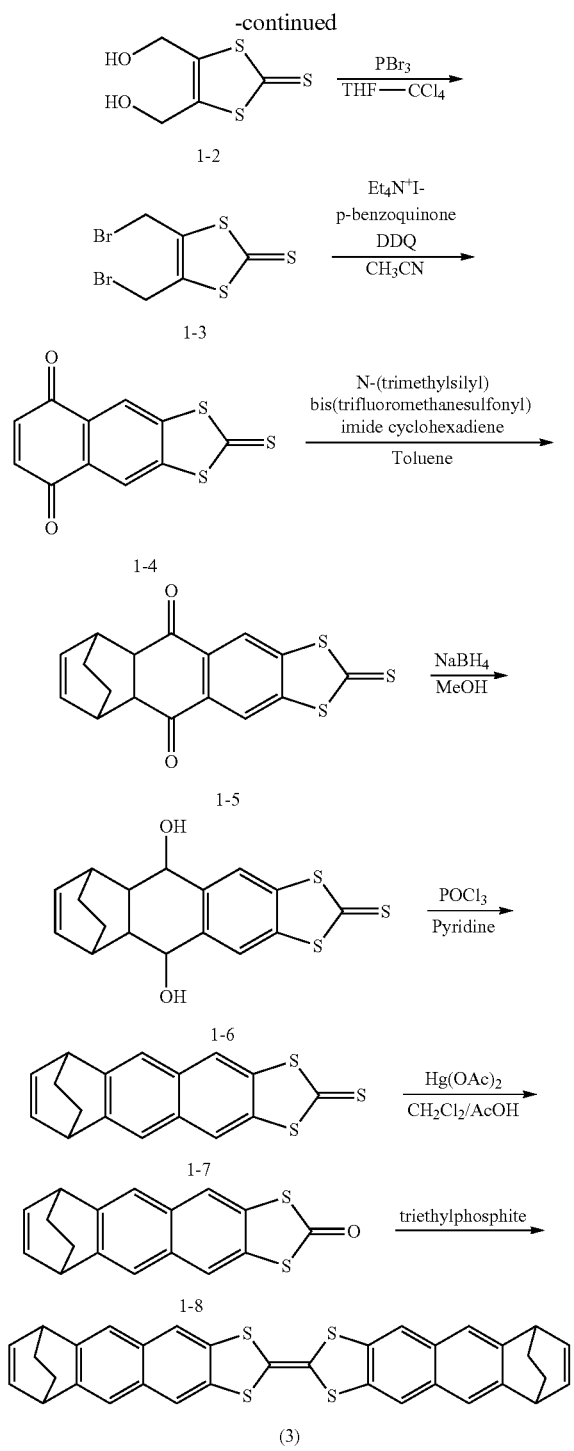

Synthesis Process <1>

Synthesis of 4,5-bis(hydroxymethyl)-1,3-dithiol-2-thione: 1-2

Methanol (100 mL) in which lithium chloride (1.00 g) had been dissolved was added dropwise to sodium borohydride (10.22 g), and then THF (50 mL) was added thereto. The resultant mixture was cooled to −10° C., and then 1,3-dithiol-2-thione-4,5-dimethyl dicarboxylate: 1-1 (10.0 g) dissolved in THF (100 mL) was added dropwise to the cooled mixture. After completion of the dropwise addition, the resultant mixture was stirred in an ice bath for 3 hours. After completion of the reaction, the reaction solution was poured into iced water (1 L) and extracted with ethyl acetate, followed by washing with a saturated saline solution. The organic layer was dried with magnesium sulfate. The magnesium sulfate was removed through filtration. Recrystallization was performed with ethyl acetate, to thereby obtain 4,5-bis(hydroxymethyl)-1,3-dithiol-2-thione: 1-2 in a yield of 88%. The target compound was identified through NMR analysis: 1H-NMR (DMSO, TMS) σ: 4.45 (d, 2H, J=5.5 Hz), 5.88 (t, 1H, J=5.5 Hz).

Synthesis Process <2>

Synthesis of 4,5-bis(bromomethyl)-1,3-dithiol-2-thione: 1-3

In a vessel, the 4,5-bis(hydroxymethyl)-1,3-dithiol-2-thione: 1-2 (5.20 g), chloroform (60 mL) and tetrahydrofuran (60 mL) were charged, and cooled in an ice bath. Phosphorus bromide (3.04 mL) dissolved in chloroform (60 mL) was added dropwise to the cooled mixture. The resultant mixture was stirred at a temperature of 5° C. or lower for 3 hours, and extracted with ethyl acetate, followed by washing with water and a saturated saline solution. The organic layer was dried with magnesium sulfate. The magnesium sulfate was removed through filtration. Recrystallization was performed with ethyl acetate, to thereby obtain 4,5-bis(bromomethyl)-1,3-dithiol-2-thione: 1-3 in a yield of 85%. The target compound was identified through NMR analysis:
1H-NMR (CDCl$_3$, TMS) σ: 4.33 (s, 4H).

Synthesis Process <3>

Synthesis of 2-thioxonaphth[2,3-d][1,3]dithiol-5,8-dione: 1-4

In a vessel, the 4,5-bis(bromomethyl)-1,3-dithiol-2-thione: 1-3 (1.10 g), tetraethylammonium iodide (0.38 g), p-benzoquinone (2.77 g), and acetonitrile (60 mL) were charged, and then refluxed for 1 hour. Thereafter, dichloro dicyano benzoquinone (1.62 g) was added in the resultant mixture, and then refluxed for 7 hours. After completion of the reflux, the solvent was distilled away, and methanol was added in the vessel, and then the precipitate was recovered through filtration. The precipitate was washed with methanol, distilled water, and ether in this order, the obtained residue was dissolved in chloroform, and then filtered. The obtained filtrate was recrystallized, to thereby obtain 2-thioxonaphth[2,3-d][1,3]dithiol-5,8-dione: 1-4 in a yield of 78%. The target compound was identified through NMR analysis:
1H-NMR (CDCl$_3$, TMS) σ: 7.04 (s, 2H), 8.15 (s, 2H).

Synthesis Process <4>

Synthesis of 6,9-dihydro-6,9-ethano-2-thioxoanthra[2,3-d][1,3]dithiol-5,10-dione: 1-5

In toluene (300 mL), the 2-thioxonaphth[2,3-d][1,3]dithiol-5,8-dione: 1-4 (0.50 g) was added, and cooled to −78° C. After cooling, N-(trimethylsilyl)bis(trifluoromethanesulfonyl)imide (1.34 g) was added to the resultant mixture, and then 1,3-cyclohexadiene (0.84 g) was further added thereto. After completion of the reaction, a 1M NaHCO$_3$ aqueous solution was added in the resultant mixture. An organic layer was separated, followed by washing with a saturated saline solution. The organic layer was dried with magnesium sulfate. The magnesium sulfate was removed through filtration. Recrystallization was performed with toluene, to thereby obtain 6,9-dihydro-6,9-ethano-2-thioxoanthra[2,3-d][1,3]dithiol-5,10-dione: 1-5 in a yield of 77%.

The target compound was identified through NMR analysis:
1H-NMR (CDCl$_3$, TMS) σ: 1.40-1.43 (m, 2H), 1.78-1.81 (m, 2H), 3.24-3.25 (m, 2H), 3.32-3.35 (m, 2H), 6.16 (dd, 2H, J$_1$=3.2 Hz, J$_2$=4.6 Hz), 8.08 (s, 2H).

Synthesis Process <5>

Synthesis of 5,10-dihydroxy-5,10-dihydro-6,9-dihydro-6,9-ethanoanthra[2,3-d][1,3]dithiol-2-thione: 1-6

In methanol (60 mL) and THF (160 mL), the 6,9-dihydro-6,9-ethano-2-thioxoanthra[2,3-d][1,3]dithiol-5,10-dione: 1-5 (0.12 g) was added, and cooled to 0° C. in an ice bath. Thereafter, sodium borohydride (0.026 g) was dissolved in the resultant mixture, and stirred for 4 hours. After completion of the reaction, the reaction solution was poured into iced water, and the precipitate was recovered through filtration. The precipitate was washed with water, and vacuum-dried to obtain 5,10-dihydroxy-5,10-dihydro-6,9-dihydro-6,9-ethanoanthra[2,3-d][1,3]dithiol-2-thione: 1-6 in a yield of 98%. The target compound was identified through NMR analysis:
1H-NMR (DMSO, TMS) σ: 1.00 (d, 2H, J$_1$=7.3 Hz), 1.42 (d, 2H, J1=7.3 Hz), 2.57 (s, 2H), 2.75 (s, 2H), 4.74 (s, 2H), 5.16 (s, 2H), 5.6 (s, 2H), 7.58 (s, 2H).

Synthesis Process <6>

Synthesis of 6,9-dihydro-6,9-ethanoanthra[2,3-d][1,3]dithiol-2-thione: 1-7

In pyridine (30 mL), the 5,10-dihydroxy-5,10-dihydro-6,9-dihydro-6,9-ethanoanthra[2,3-d][1,3]dithiol-2-thione: 1-6 (1.03 g) was dissolved, and cooled to 0° C. in an ice bath. Thereafter, phosphonyl chloride (0.81 mL) was added in the cooled mixture, and stirred for 2 hours. After completion of the reaction, the mixture was poured into iced water, and then the obtained precipitate was recovered through filtration.

The precipitate was washed with water, dissolved in chloroform, and then dried with magnesium sulfate. Thereafter, the magnesium sulfate was removed through filtration. The solvent was distilled away, and column chromatography was performed to separate 6,9-dihydro-6,9-ethanoanthra[2,3-d][1,3]dithiol-2-thione: 1-7 in a yield of 92%. 1H-NMR (CDCl$_3$, TMS) σ: 1.55-1.57 (m, 2H), 1.66-1.69 (m, 2H), 4.04-4.06 (m, 2H), 6.56-6.57 (dd, 2H, J$_1$=3.1 Hz, J$_2$=4.6 Hz), 7.54 (s, 2H), 7.85 (s, 2H).

Synthesis Process <7>

Synthesis of 6,9-dihydro-6,9-ethanoanthra[2,3-d][1,3]dithiol-2-one: 1-8

In chloroform (90 mL), the 6,9-dihydro-6,9-ethanoanthra[2,3-d][1,3]dithiol-2-thione: 1-7 (0.92 g) was dissolved, and to the resultant solution mercuric acetate dissolved in acetic acid was added dropwise, and stirred at room temperature for 4 hours. After completion of the reaction, the reactant was subjected to celite filtration, followed by washing with chloromethyl. The filtrate was washed with a NaHCO₃ aqueous solution, and distilled water, and then dried with magnesium sulfate. After the magnesium sulfate was removed through filtration, the solvent was distilled away, to thereby obtain 6,9-dihydro-6,9-ethanoanthra[2,3-d] [1,3]dithiol-2-one: 1-8 in a yield of 76%. 1H-NMR (CDCl₃, TMS) σ: 1.54-1.56 (m, 2), 1.66-1.69 (m, 2H), 4.03-4.06 (m, 2H), 6.56-6.57 (dd, 2H, $J_1$=3.1 Hz, $J_2$=4.6 Hz), 7.51 (s, 2H), 7.86 (s, 2H).

Through analysis of 6,9-dihydro-6,9-ethanoanthra[2,3-d] [1,3]dithiol-2-one: 1-8 by infrared spectroscopy (KBr), absorption at 1718 cm⁻¹ attributed to the C=O bond was confirmed.

Synthesis Process <8>

Synthesis of bis(6,9-dihydro-6,9-ethanoanthra[2,3-d])tetrathiafulvalene: (3)

The 6,9-dihydro-6,9-ethanoanthra[2,3-d] [1,3]dithiol-2-one: 1-8 (0.20 g) was mixed with triethyl phosphonate (2.00 mL), and stirred at 140° C. for 9 hours. The reaction solution was left to cool, filtered, and washed with methanol. Then, the reaction solution was further washed with chloroform to thereby obtain bis(6,9-dihydro-6,9-ethanoanthra[2,3-d]) tetrathiafulvalene: (3) in a yield of 67%.

Mass spectrometry: GC-MS m/z=281 [M²⁺]
Elemental Analysis

| | Elemental analysis | |
|---|---|---|
| | Found (% by mass) | Calculated (% by mass) |
| C | 72.21 | 72.82 |
| H | 3.84 | 4.31 |

Figure 2:
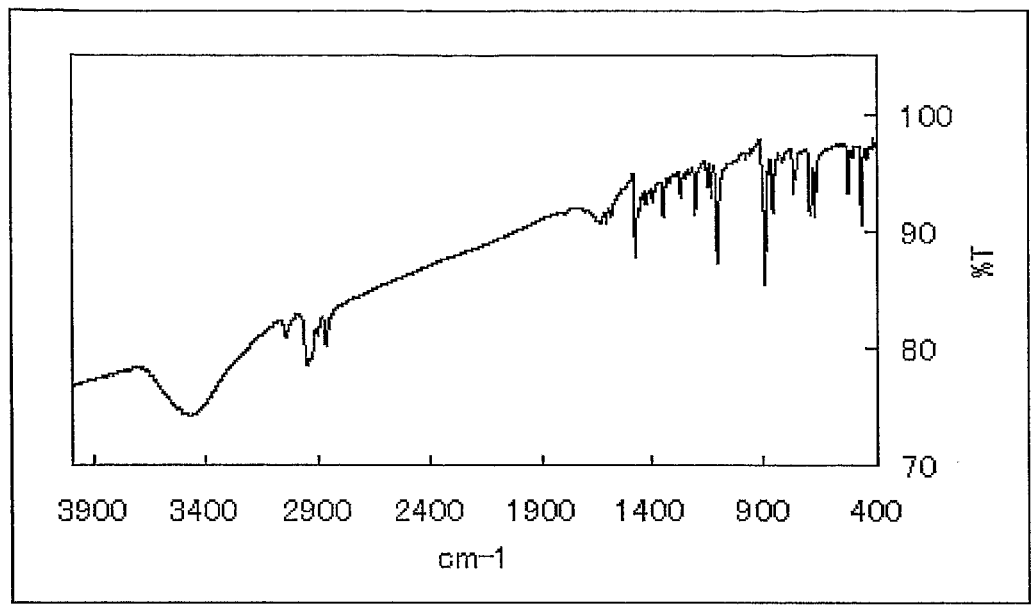
FIG. 2 shows an IR spectrum of bis(6,9-dihydro-6,9-ethanoanthra[2,3-d])tetrathiafulvalene. "% T" of the vertical axis represents transmission.

The bis(6,9-dihydro-6,9-ethanoanthra[2,3-d])tetrathiafulvalene: (3) was analyzed by infrared spectroscopy (KBr), and the result is shown in FIG. 2.

Example 2

An organic film was produced using the bis(6,9-dihydro-6,9-ethanoanthra[2,3-d])tetrathiafulvalene: tetrathiafulvalene derivative (3) synthesized in Example 1 by the method described below.

A N-type silicon substrate including a thermally-oxidized film having a film thickness of 300 nm was immersed and washed in a concentrated sulfuric acid for 24 hours, and then immersed in a toluene solution (1 mM) of silane coupling agent (octyltrichlorosilane). Then, the substrate subjected to ultrasonic treatment for 5 minutes so as to form a monomolecular film on a surface of a silicon oxide film.

Over the substrate prepared by the above method, the bis (6,9-dihydro-6,9-ethanoanthra[2,3-d])tetrathiafulvalene: (3) obtained in Example 1 was vapor deposited under the conditions of a back pressure of up to 10⁻⁴ Pa, a deposition rate of 0.1 Å/s, and a semiconductor film thickness of 50 nm, to thereby obtain a smooth and uniform organic film.

The ionization potential of the organic film was measured by photoelectron spectrometer AC-2 (manufactured by RIKEN KEIKI Co., Ltd., standard sample: a Au-deposited film, dose of irradiated light: 5.0 nW). As a result, the ionization potential of the bis(6,9-dihydro-6,9-ethanoanthra[2,3-d])tetrathiafulvalene: (3) was found to be 4.9 eV.

Example 3

Synthesis of bis(anthra[2,3-d])tetrathiafulvalene: tetrathiafulvalene derivative (1)

A synthesis route of compound (1) is as follows.

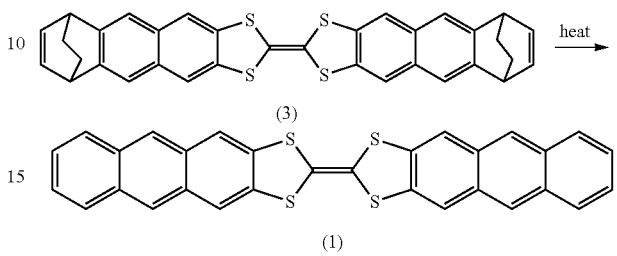

Synthesis Process <9>

Synthesis of bis(anthra[2,3-d])tetrathiafulvalene: tetrathiafulvalene derivative (1)

A three-necked flask was purged with nitrogen and then charged with the bis(6,9-dihydro-6,9-ethanoanthra[2,3-d]) tetrathiafulvalene: tetrathiafulvalene derivative (3) (0.20 g). Subsequently, the flask was placed on a hot plate set at 280° C. Yellow powder of tetrathiafulvalene derivative (3) was changed in a few minutes to red powder of bis(anthra[2,3-d]) tetrathiafulvalene: tetrathiafulvalene derivative (1) (yield: 99%).

| | Elemental analysis | |
|---|---|---|
| | Found (% by mass) | Calculated (% by mass) |
| C | 71.15 | 71.39 |
| H | 2.77 | 3.20 |

Figure 3:
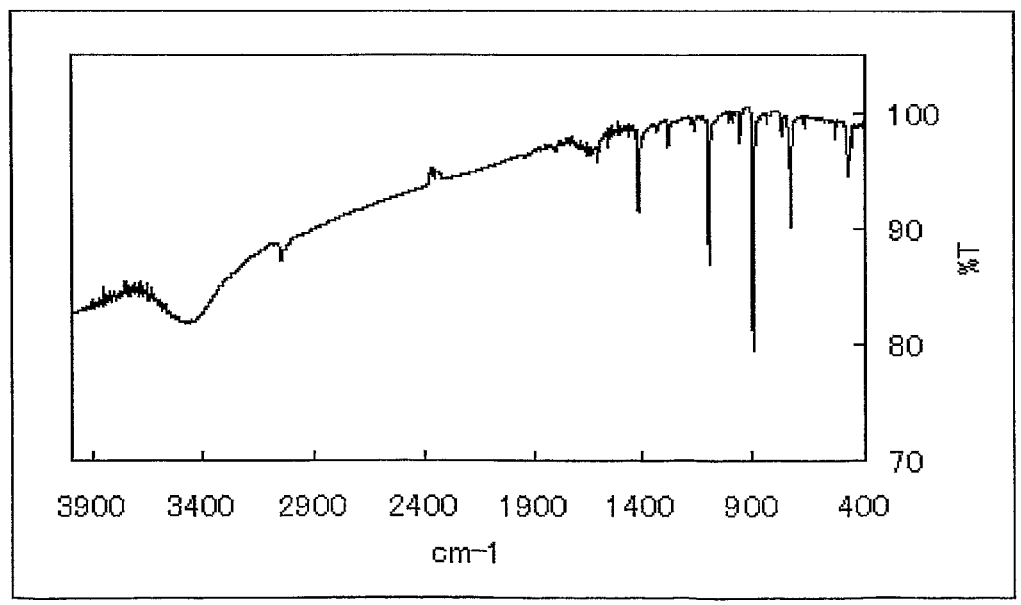
FIG. 3 shows an IR spectrum of bis(anthra[2,3-d])tetrathiafulvalene. "% T" of the vertical axis represents transmission.

The bis(anthra[2,3-d])tetrathiafulvalene was analyzed by infrared spectroscopy (KBr), and the result is shown in FIG. 3.

Example 4

An organic film was produced using the bis(anthra[2,3-d]) tetrathiafulvalene: tetrathiafulvalene derivative (1) synthesized in Example 3 by the method described below.

A N-type silicon substrate including a thermally-oxidized film having a film thickness of 300 nm was immersed and washed in a concentrated sulfuric acid for 24 hours. Then, the substrate was immersed in a toluene solution (1 mM) of silane coupling agent (octyltrichlorosilane), and subjected to ultrasonic treatment for 5 minutes so as to form a monomolecular film on a surface of a silicon oxide film.

Over the substrate prepared by the above method, the bis (anthra[2,3-d])tetrathiafulvalene: tetrathiafulvalene derivative (1) obtained in Example 3 was vapor deposited under the conditions of a back pressure of up to 10⁻⁴ Pa, a deposition rate of 0.1 Å/s, and a semiconductor film thickness of 50 nm, to thereby obtain a smooth and uniform organic film.

The ionization potential of the organic film was measured by photoelectron spectrometer AC-2 (manufactured by RIKEN KEIKI Co., Ltd., standard sample: a Au-deposited film, dose of irradiated light: 5 nW). As a result, the ionization potential of the bis(anthra[2,3-d])tetrathiafulvalene: tetrathiafulvalene derivative (1) was found to be 4.9 eV.

Figure 4:
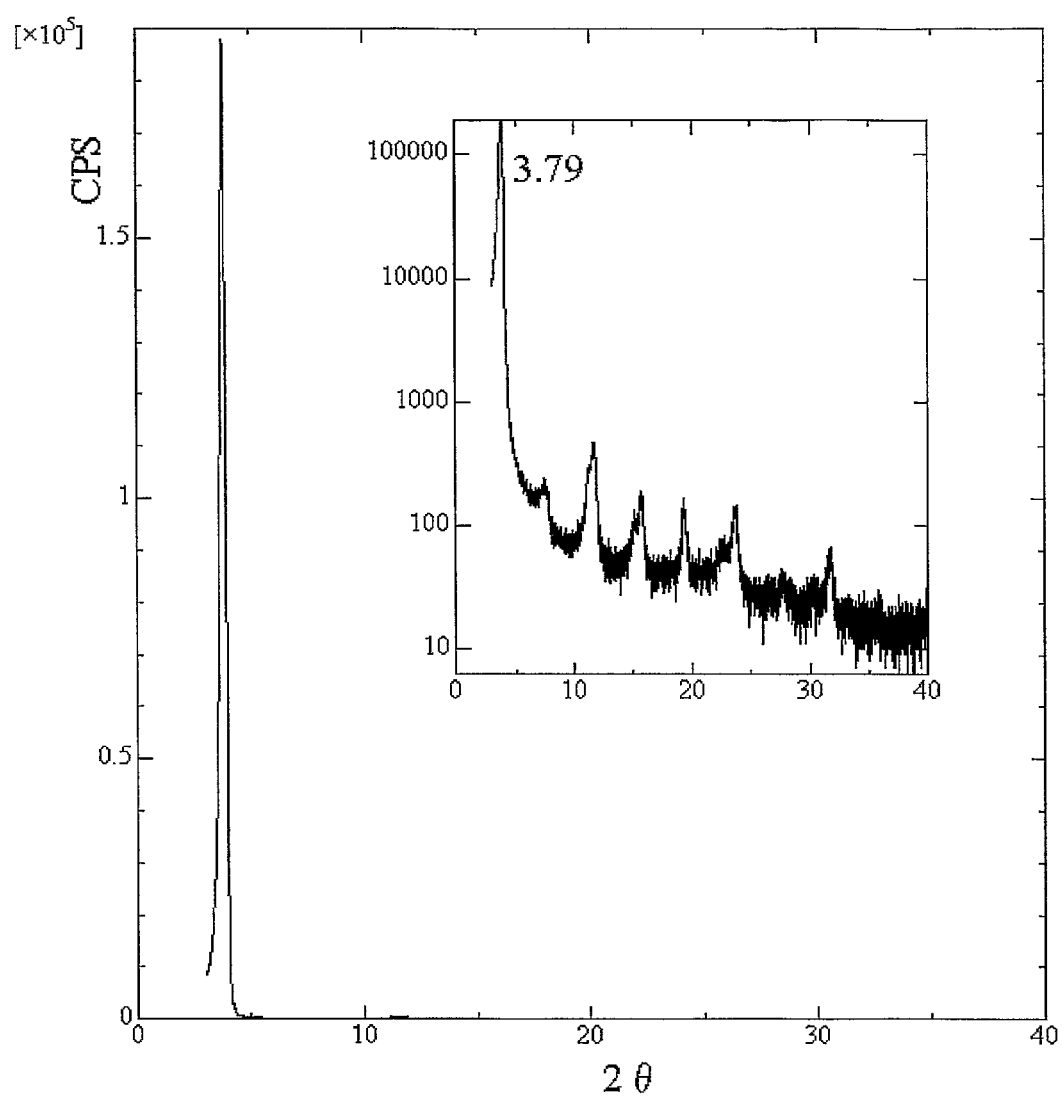
FIG. 4 shows an out-of-plane X ray diffraction pattern of a deposited film of bis(anthra[2,3-d])tetrathiafulvalene.
Figure 5:
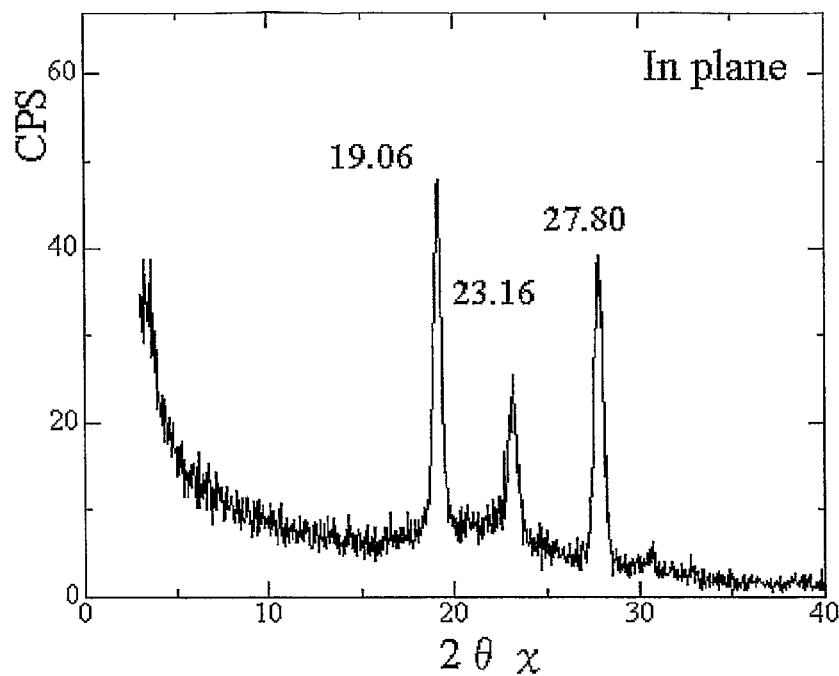
FIG. 5 shows an in-plane X ray diffraction pattern of the deposited film of bis(anthra[2,3-d])tetrathiafulvalene.

An out-of-plane X ray diffraction pattern of the organic film is shown in FIG. 4, and an in-plane X ray diffraction pattern of the organic film is shown in FIG. 5.

Example 5

A field-effect transistor having a structure shown in FIG. 1D was produced using the bis(anthra[2,3-d])tetrathiafulvalene: tetrathiafulvalene derivative (1) synthesized in Example 3 by the method described below.

A N-type silicon substrate including a thermally-oxidized film having a film thickness of 300 nm was immersed and washed in a concentrated sulfuric acid for 24 hours. Then, the substrate was immersed in a toluene solution (1 mM) of silane coupling agent (phenyltrichlorosilane), and subjected to ultrasonic treatment for 5 minutes so as to form a monomolecular film on a surface of a silicon oxide film.

Over the substrate prepared by the above method, the bis (anthra[2,3-d])tetrathiafulvalene: tetrathiafulvalene derivative (1) obtained in Example 1 was vapor deposited under the conditions of a back pressure of up to $10^{-4}$ Pa, a deposition rate of 0.1 Å/s, and a semiconductor film thickness of 50 nm, to thereby obtain an organic semiconductor layer.

Over the organic semiconductor layer Au was vapor deposited via a shadow mask under the conditions of a back pressure of up to $10^{-4}$ Pa, a deposition rate of 1 Å/s to 2 Å/s and a film thickness of 50 nm, to thereby form source and drain electrodes having a channel length of 50 μm and channel width of 2 mm. The organic semiconductor layer and silicon oxide film in a region other than the electrodes was removed by scraping, and a conductive paste (manufactured by Fujikura Kasei Co., Ltd.) was applied in the region and the solvent was dried. Through the region, voltage was applied to the silicon substrate serving as the gate electrode, to thereby produce a field-effect transistor (FET) element.

Figure 6:
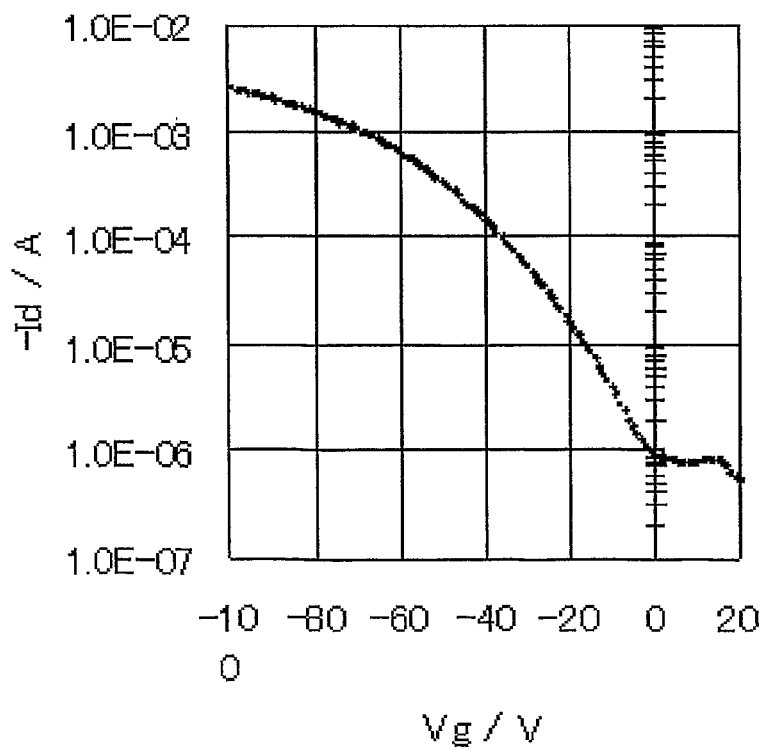
FIG. 6 shows transfer characteristics of an example of a thin-film transistor using bis(anthra[2,3-d])tetrathiafulvalene.
Figure 7:
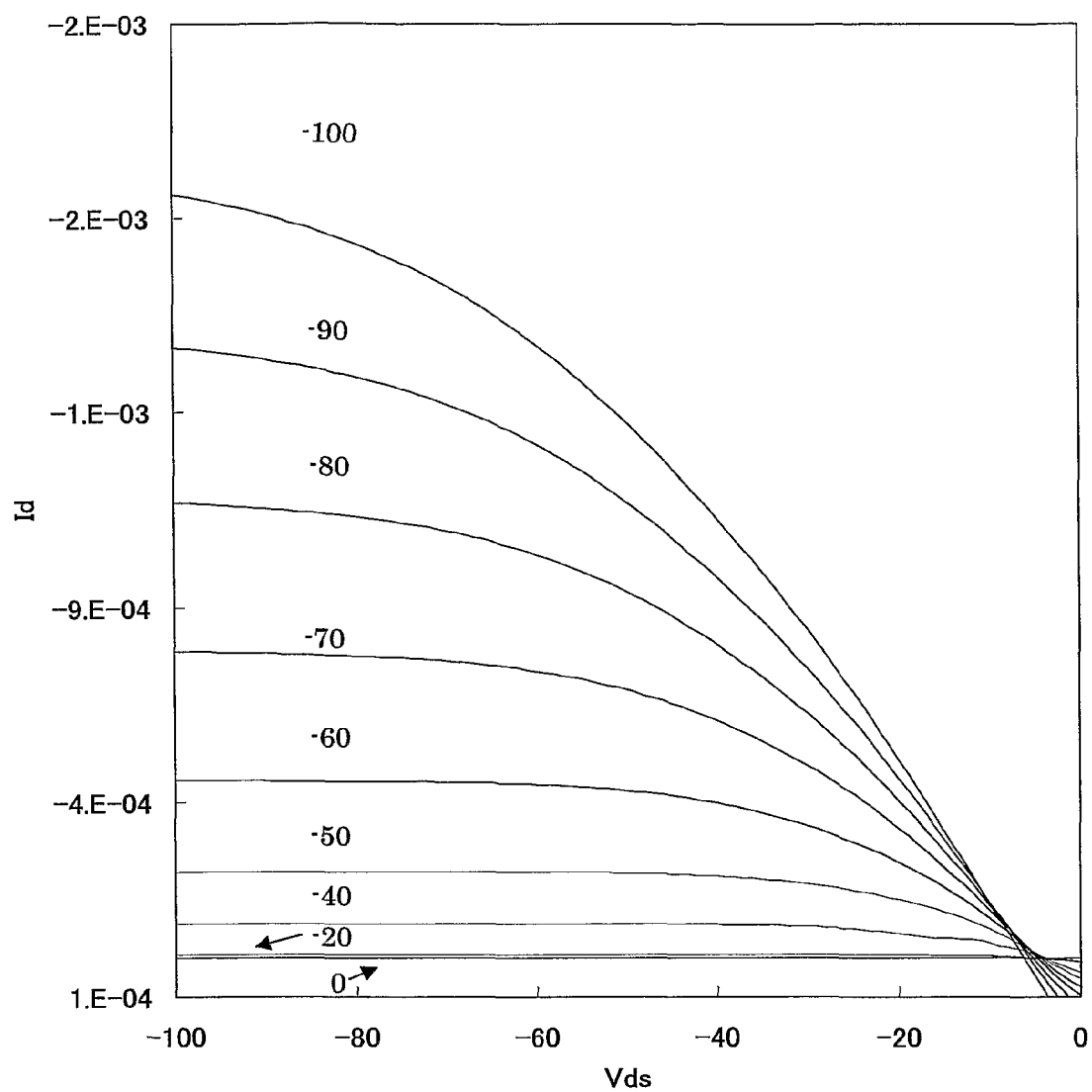
FIG. 7 shows output characteristics of an example of the thin-film transistor using bis(anthra[2,3-d])tetrathiafulvalene.

The electrical characteristics of the FET element was evaluated by a semiconductor parameter analyzer 4156C (manufactured by Agilent Technologies). The FET element exhibited a property as a p-type transistor element. The transfer characteristics of the organic thin-film transistor is shown in FIG. 6. The output characteristics of the organic thin-film transistor is shown in FIG. 7. From the saturation region of the transfer characteristics, a field-effect mobility was obtained.

The field-effect mobility (μ) of the organic thin-film transistor was calculated by the following equation.

$$Ids = \mu C in W (Vg-Vth)2/2 L$$

In the equation, Cin is a capacitance per unit area of a gate insulating film, W is a channel width, L is a channel length, Vg is a gate voltage, Ids is a source-drain current, μ is a field effect mobility and Vth is a gate threshold voltage at which a channel begins to be formed.

The field-effect mobility of the produced organic thin-film transistor was 0.96 cm$^2$/Vs.

Figure 8:
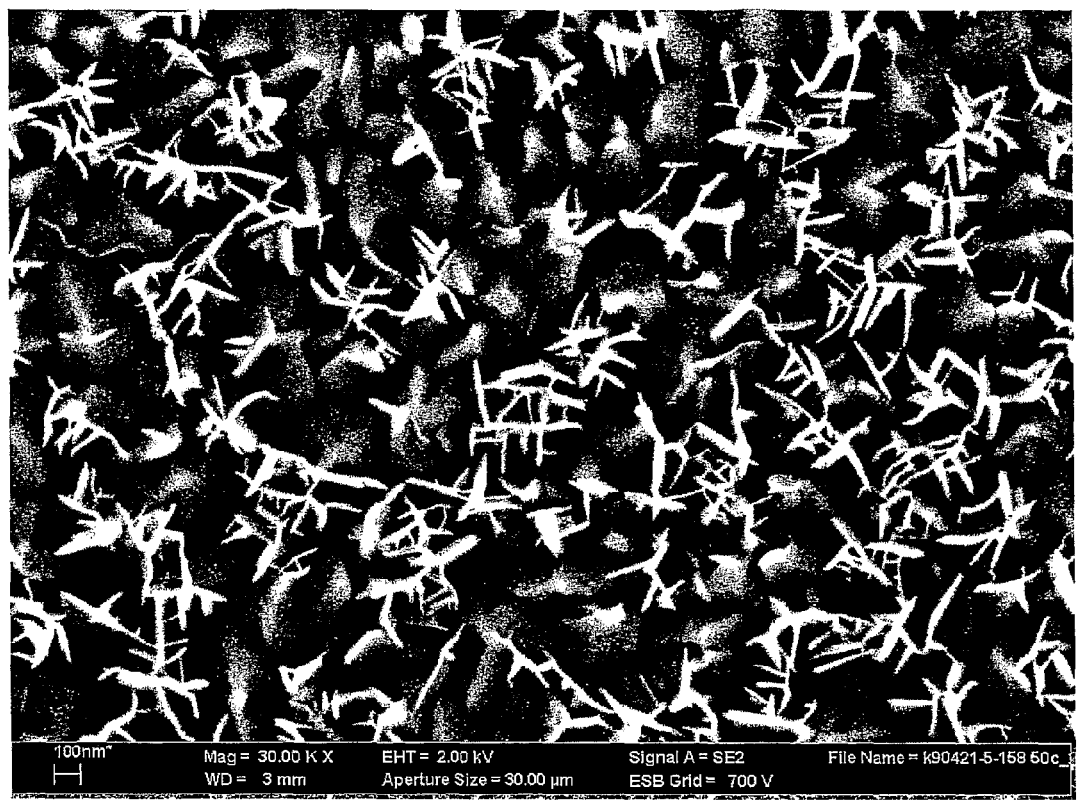
FIG. 8 shows a SEM image of a channel region of the thin-film transistor using bis(anthra[2,3-d])tetrathiafulvalene.

A SEM image of the channel region of the produced field-effect transistor is shown in FIG. 8.

Example 6

Synthesis of bis{6,9-dihydro-6,9-(11,11-dimethyl-ethanoanthra)[2,3-d]}tetrathiafulvalene: tetrathiafulvalene derivative (4)

Compound (4) was synthesized using compound (1-4) of Example 1.

A synthesis route of compound (4) is as follows.

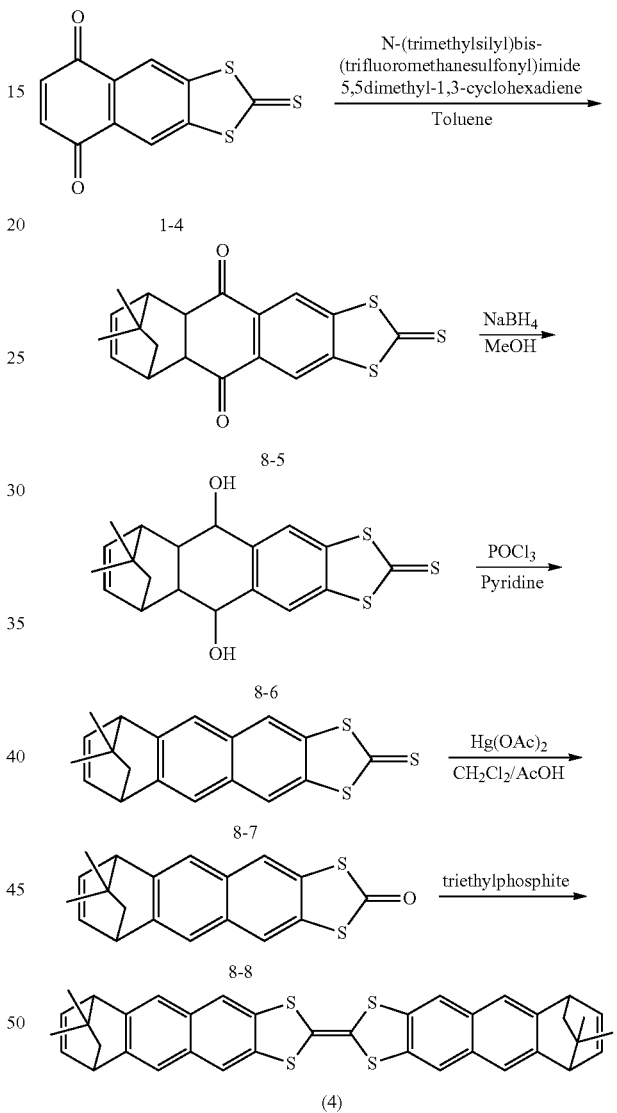

Synthesis of 6,9-dihydro-6,9-(11,11-dimethyl-ethano)-2-thioxoanthra[2,3-d] [1,3]dithiol-5,10-dione: 8-5

In toluene (1,000 mL), the 2-thioxonaphth[2,3-d] [1,3] dithiol-5,8-dione: 1-4 (1.87 g) was added and cooled to −78° C. Thereafter, in the resultant mixture N-(trimethylsilyl)bis (trifluoromethanesulfonyl)imide (3.06 g) was added, and then 5,5-dimethyl-1,3-cyclohexadiene (5.0 g) was further added. After completion of the reaction, a 1M NaHCO$_3$ aqueous solution was added in the resultant mixture. An organic layer was separated, followed by washing with a saturated saline solution, and then the organic layer was dried with magnesium sulfate. The magnesium sulfate was removed through filtration. Recrystallization was performed with toluene, to thereby obtain 6,9-dihydro-6,9-(11,11-dimethylethano)-2-thioxoanthra[2,3-d][1,3]dithiol-5,10-dione: 8-5 in a yield of 70%. The target compound was identified through NMR analysis: 1H-NMR (CDCl$_3$, TMS) σ: 0.89 (s, 3H), 1.19 (s, 3H), 2.97-2.99 (m, 1H), 3.22 (d, 2H, J=7.4 Hz), 3.53-3.56 (m, 1H), 6.06 (t, 1H, J=6.6 Hz), 6.23 (t, 1H, J=6.6 Hz), 8.08 (s, 2H).

The bis{6,9-dihydro-6,9-(11,11-dimethylethanoanthra)[2,3-d]}tetrathiafulvalene: tetrathiafulvalene derivative (4) was obtained using the obtained compound 8-5 by the same process as Synthesis Processes <5> to <8> in Example 1. The target compound was identified through NMR analysis: 1H-NMR (CDCl$_3$, TMS) σ: 0.66 (s, 3H), 1.08 (s, 3H), 1.33 (d, 1, J=6.3 Hz), 1.49 (d, 2H, J=6.3 Hz), 3.41-3.42 (m, 1H), 3.86-3.87 (m, 1H), 7.37 (s, 2H), 7.61 (s, 2H).

| Elemental analysis | | |
|---|---|---|
| | Found (% by mass) | Calculated (% by mass) |
| C | 73.88 | 71.98 |
| H | 4.77 | 5.23 |

Figure 9:
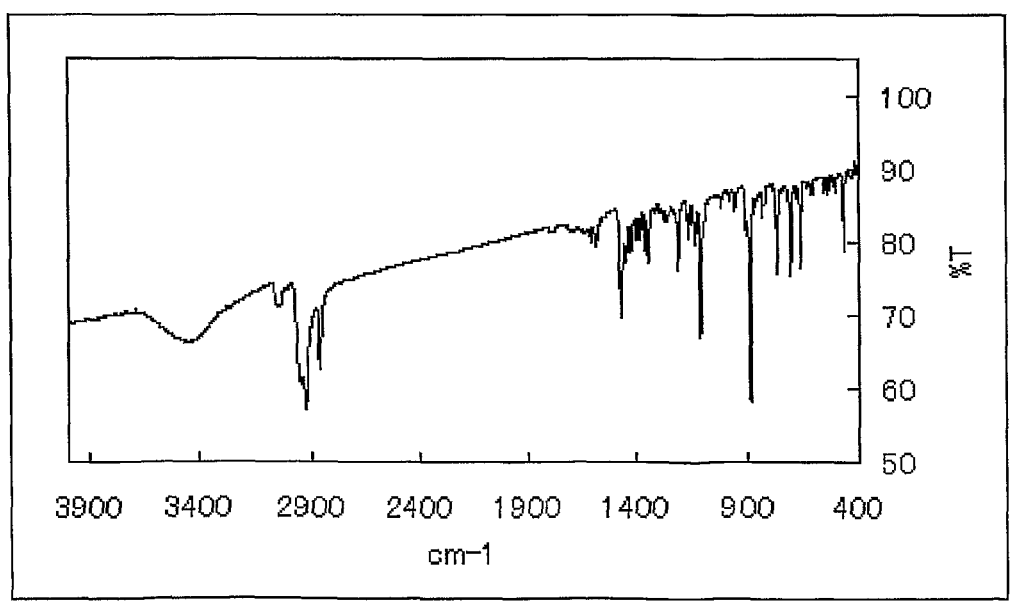
FIG. 9 shows an IR spectrum of bis{(6,9-dihydro-6,9-(11,11-dimethylethanoanthra[2,3-d]}tetrathiafulvalene. "% T" of the vertical axis represents transmission.

The bis{6,9-dihydro-6,9-(11,11-dimethylethanoanthra)[2,3-d]}tetrathiafulvalene: tetrathiafulvalene derivative (4) was analyzed by infrared spectroscopy (KBr), and the result is shown in FIG. 9.

Example 7

An organic film was produced using the bis{6,9-dihydro-6,9-(11,11-dimethylethanoanthra)[2,3-d]}tetrathiafulvalene: tetrathiafulvalene derivative (4) synthesized in Example 6 in the same process as in Example 2.

The ionization potential of the produced organic film was measured by photoelectron spectrometer AC-2 (manufactured by RIKEN KEIKI Co., Ltd., standard sample: a Au-deposited film, dose of irradiated light: 25 nW). As a result, the ionization potential of the bis{6,9-dihydro-6,9-(11,11-dimethylethanoanthra)[2,3-d]}tetrathiafulvalene: tetrathiafulvalene derivative (4) was found to be 5.0 eV.

Example 8

Synthesis of bis(benzo[g]quinoxaline)tetrathiafulvalene: tetrathiafulvalene derivative (23)

A synthesis route of compound (23) is as follows.

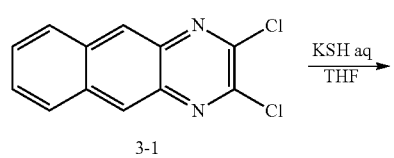

3-1

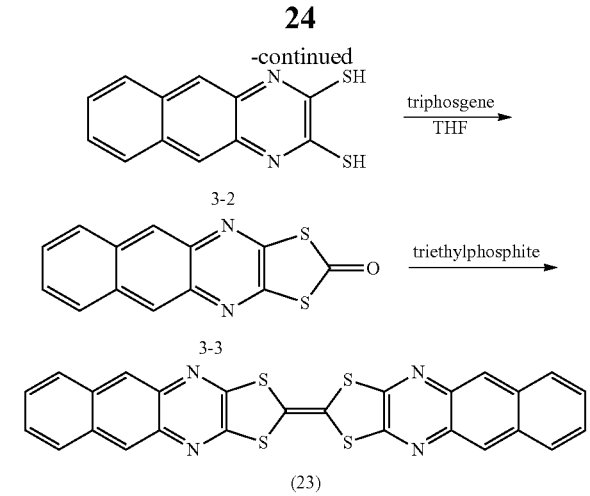

Synthesis Process <10>

Synthesis of benzo[g]quinoxaline-2,3-dithiol: 3-2

In tetrahydrofuran (100 mL), 2,3-dichlorobenzo[g]quinoxaline: 3-1 (0.43 g) was added, and 10% by mass to 20% by mass aqueous potassium hydrosulfide solution (2.83 g) was further added. The solution was stirred at room temperature for 16 hours. The reaction solution was poured into distilled water (400 mL), and acidified with hydrochloric acid. The precipitate was washed with distilled water, and then washed with chloroform, to thereby obtain benzo[g]quinoxaline-2,3-dithiol: 3-2 in a yield of 98%.

The target compound was identified through NMR and MS analysis: 1H-NMR (DMSO, TMS) σ: 7.48 (dd, 2H, J1=6.3, J2=3.2 Hz), 7.84 (s, 2H), 7.91 (dd, 2H, J1=6.3, J2=3.5 Hz), GC-MS m/z=244.

Synthesis Process <11>

Synthesis of benzo[g][1,3]dithiolo[4,5-b]quinoxaline-2-one: 3-3

In tetrahydrofuran (200 mL), the benzo[g]quinoxaline-2,3-dithiol: 3-2 (0.29 g) was added, and triphosgene (0.60 g) was further added. The solution was stirred at room temperature for 18 hours. The reaction solution was poured into distilled water (400 mL), and the precipitate was filtered.

Thereafter, the filtered precipitate was sequentially washed with distilled water, and methanol, and then dissolved in chloroform. The solution was subjected to column chromatography using chloroform as an eluant to thereby separate benzo[g][1,3]dithiolo[4,5-b]quinoxaline-2-one: 3-3 in a yield of 40%.

The target compound was identified through NMR, MS, and IR analysis: 1H-NMR (DMSO, TMS) σ: 7.64 (dd, 2H, J1=6.5, J2=3.2 Hz), 8.12 (dd, 2H, J1=6.5, J2=3.2 Hz), 8.59 (s, 2H) GC-MS m/z=270. Through analysis of benzo[g][1,3]dithiolo[4,5-b]quinoxaline-2-one: 3-3 by infrared spectroscopy (KBr), absorption at 1728 cm$^{-1}$ attributed to the C=O bond was confirmed.

Synthesis Process <12>

Synthesis of bis(benzo[g]quinoxaline)tetrathiafulvalene: tetrathiafulvalene derivative (23)

The benzo[g][1,3]dithiolo[4,5-b]quinoxaline-2-one: 3-3 (0.21 g) was mixed with triethyl phosphonate (6.00 mL), and stirred at 140° C. for 9 hours. The reaction solution was left to cool, filtered, and washed with methanol. Then, the reaction solution was further washed with chloroform to thereby obtain bis(benzo[g]quinoxaline)tetrathiafulvalene: tetrathiafulvalene derivative (23) in a yield of 91%.

Mass spectrometry: GC-MS m/z=508

Figure 10:
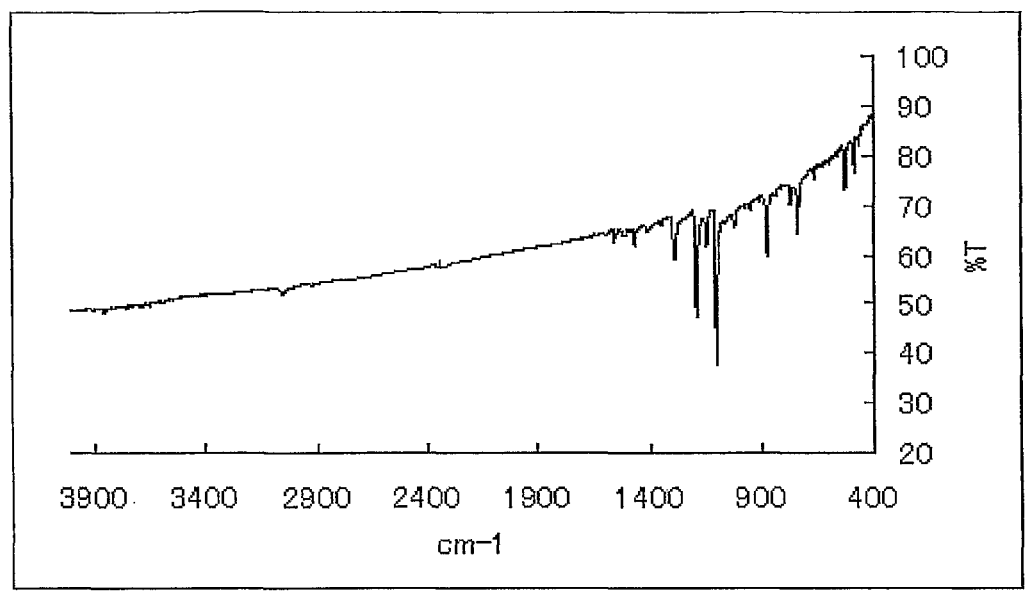
FIG. 10 shows an IR spectrum of bis(benzo[g]quinoxaline)tetrathiafulvalene. "% T" of the vertical axis represents transmission.

Infrared spectroscopy (KBr) was performed. The result is shown in FIG. 10.

Example 9

An organic film was produced using the bis(benzo[g]quinoxaline)tetrathiafulvalene: tetrathiafulvalene derivative (23) synthesized in Example 8 by the same process as in Example 2.

The ionization potential of the organic film was measured by photoelectron spectrometer AC-2 (manufactured by RIKEN KEIKI Co., Ltd., standard sample: a Au-deposited film, dose of irradiated light: 50 nW). As a result, the ionization potential of the bis(benzo[g]quinoxaline)tetrathiafulvalene: (23) was found to be 5.5 eV.

Example 10

Figure 1D:
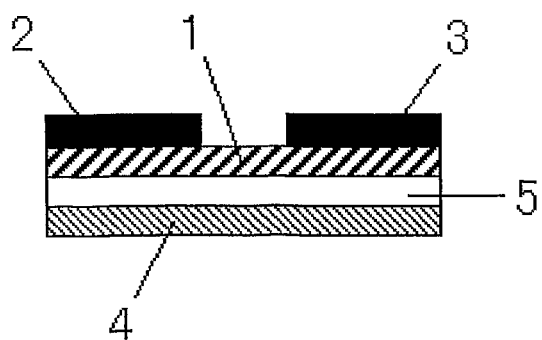
Figure 11:
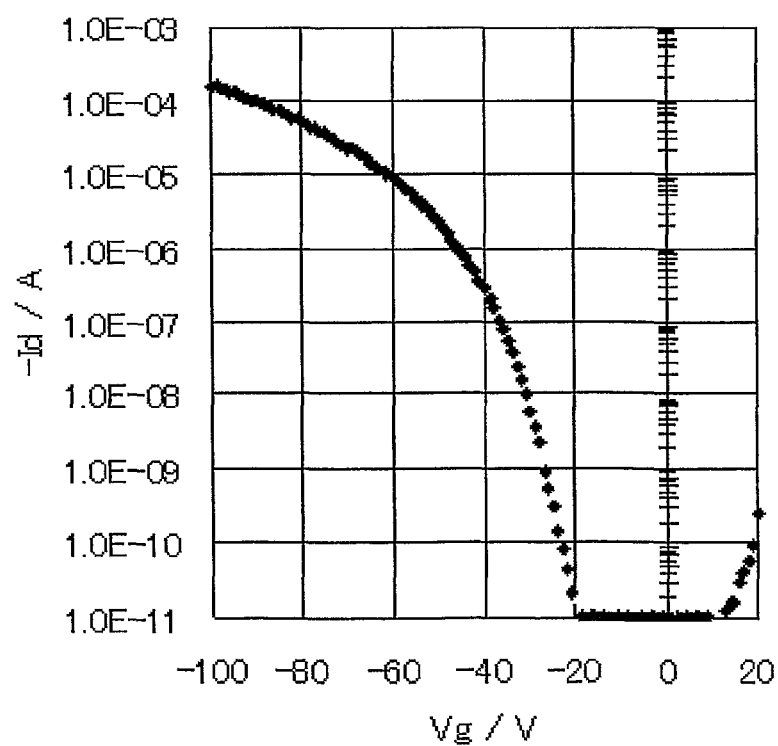
FIG. 11 shows transfer characteristics of an example of a thin-film transistor using bis(benzo[g]quinoxaline)tetrathiafulvalene.
Figure 12:
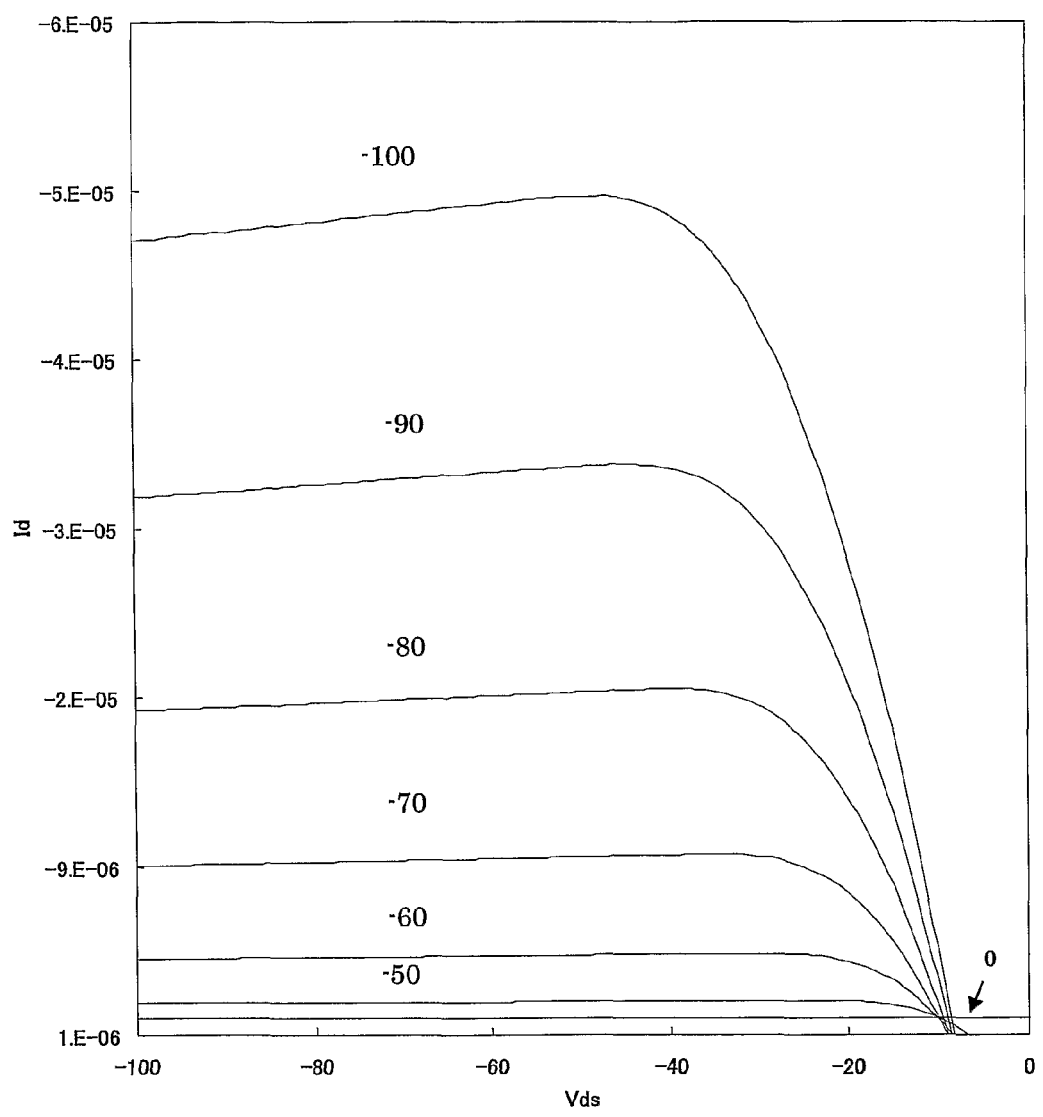
FIG. 12 shows output characteristics of an example of the thin-film transistor using bis(benzo[g]quinoxaline)tetrathiafulvalene.

A field-effect transistor having a structure shown in FIG. 1D was produced using the bis(benzo[g]quinoxaline)tetrathiafulvalene: tetrathiafulvalene derivative (23) synthesized in Example 8 by the same process as in Example 5. The electrical characteristics of the obtained field-effect transistor (FET) element was evaluated by a semiconductor parameter analyzer 4156C (manufactured by Agilent Technologies). The FET element exhibited a property as a p-type transistor element. The transfer characteristics of the organic thin-film transistor is shown in FIG. 11. The output characteristics of the organic thin-film transistor is shown in FIG. 12. From the saturation region of the transfer characteristics, a field-effect mobility was obtained.

The field-effect mobility of the produced organic thin-film transistor was 0.50 cm$^2$/Vs.

Comparative Example 1

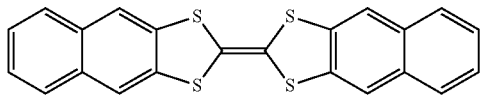 [SMILES: c1ccc2cc3c(cc2c1)SC(=C1Sc2cc4ccccc4cc2S1)S3]

An organic film was produced using bisnaphthotetrathiafulvalene expressed by the above chemical formula by the same process as in Example 2.

The ionization potential of the produced organic film was measured by photoelectron spectrometer AC-2 (manufactured by RIKEN KEIKI Co., Ltd., standard sample: a Au-deposited film, dose of irradiated light: 5.0 nW). As a result, the ionization potential of the bisnaphthotetrathiafulvalene was found to be 4.7 eV.

REFERENCE SIGNS LIST

1: organic semiconductor layer
2: source electrode
3: drain electrode
4: gate electrode
5: gate insulating film

The invention claimed is:

1. A tetrathiafulvalene derivative of Formula (I):

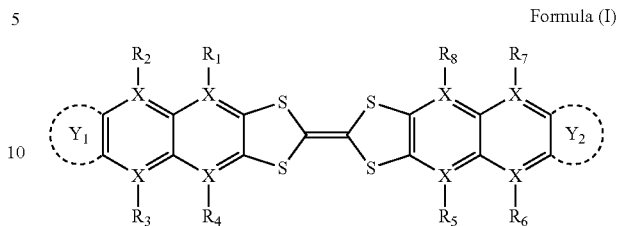

Formula (I)

wherein each X is independently a carbon atom, or a nitrogen atom, and
$R_1$ to $R_8$ are each independently a hydrogen atom, a halogen atom, a substituted or unsubstituted alkyl group, a substituted or unsubstituted alkoxy group, or a substituted or unsubstituted thioalkoxy group when an adjacent X is a carbon atom,
$R_1$ to $R_8$ each independently do not exist when an adjacent X is a nitrogen atom, and
$Y_1$ and $Y_2$ are each independently of Formula (II) or (III):

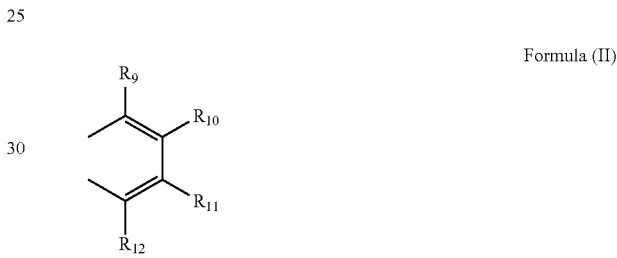

Formula (II)

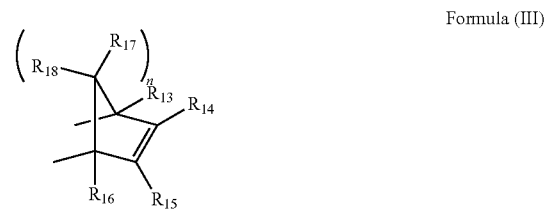

Formula (III)

wherein $R_9$ to $R_{18}$ are each independently a hydrogen atom, a halogen atom, a substituted or unsubstituted alkyl group, a substituted or unsubstituted alkoxy group, or a substituted or unsubstituted thioalkoxy group,
n is an integer of 1 to 3, and
when n is 2 or 3, each $R_{17}$ is independently selected and each $R_{18}$ is independently selected.

2. An organic film comprising the tetrathiafulvalene derivative as claimed in claim 1.

3. An organic transistor comprising the tetrathiafulvalene derivative as claimed in claim 1.

4. The tetrathiafulvalene derivative of claim 1, wherein the tetrathiafulvalene derivative is a structure of at least one formula selected from the group consisting of Structural Formulas (1) through (11), (23) through (33), and (45) through (55):

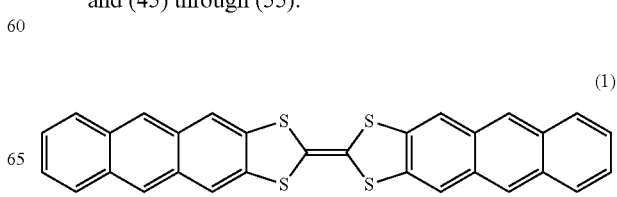

(1)

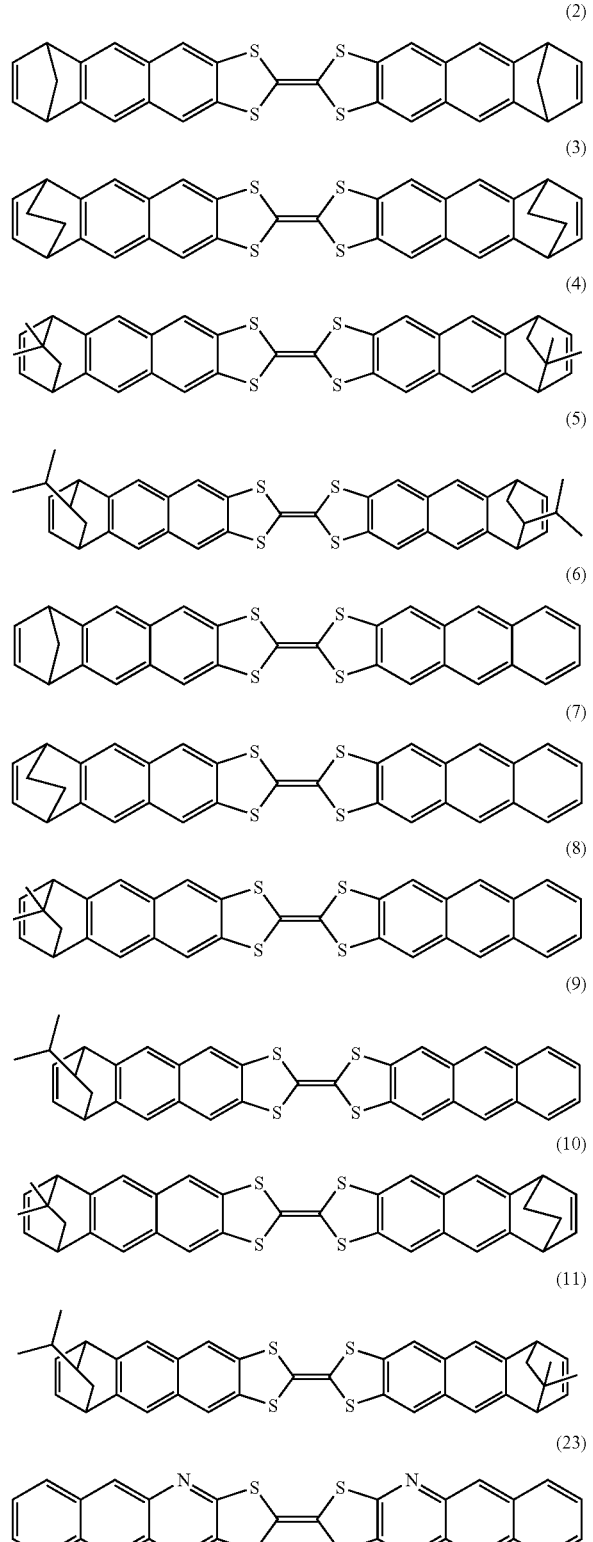
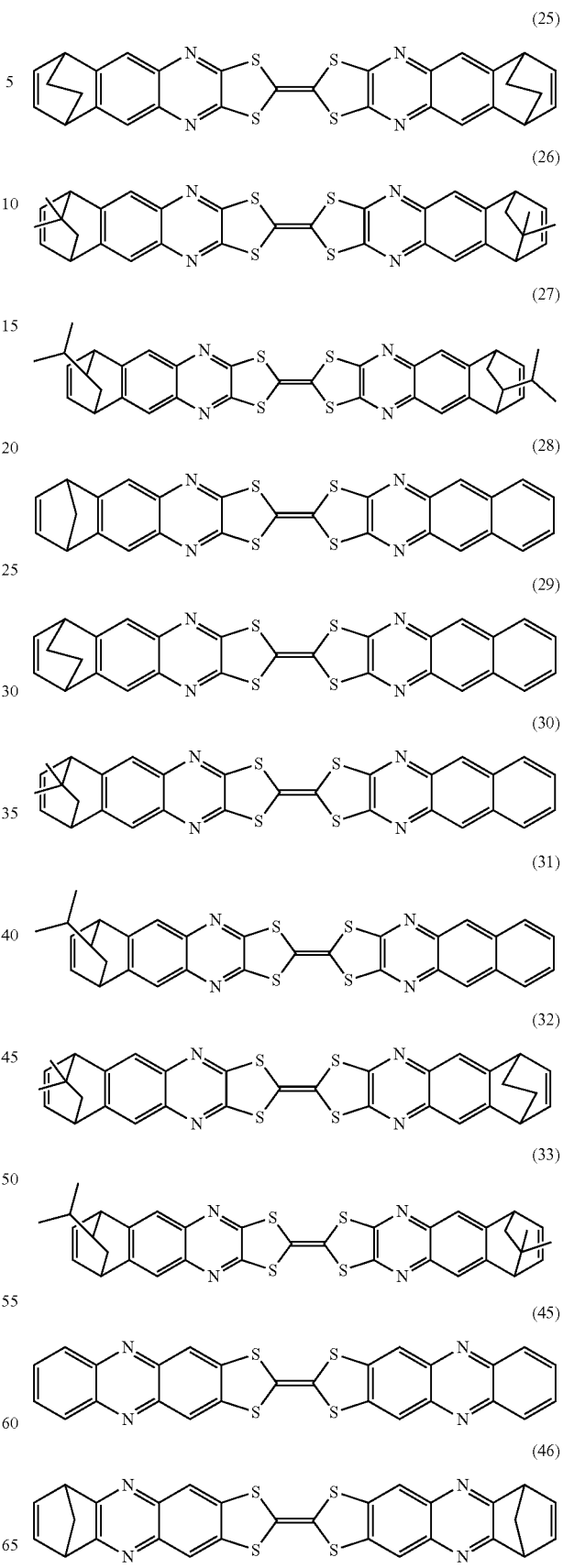

(47)
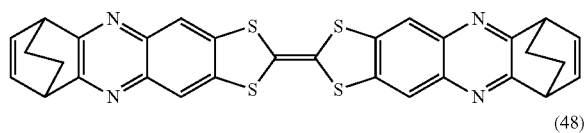
(48)
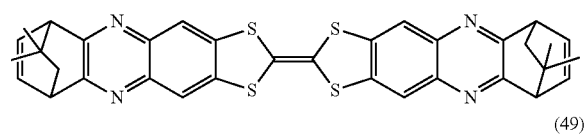
(49)
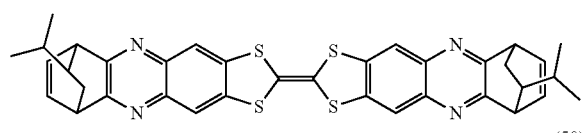
(50)
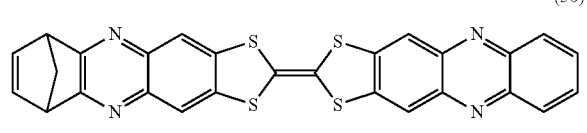
(51)
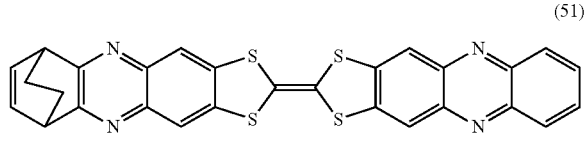
(52)
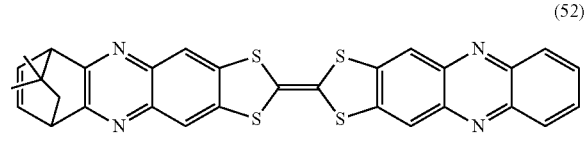
(53)
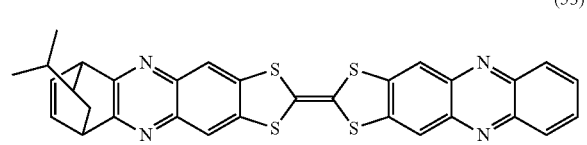
(54)
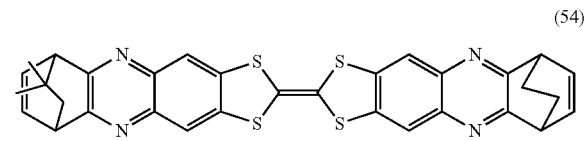
(55)
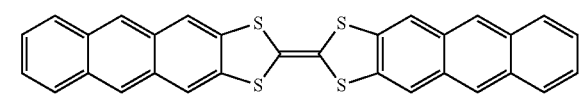
5. The tetrathiafulvalene derivative according to claim 4, wherein the tetrathiafulvalene derivative is a structure of at least one formula selected from the group consisting of Structural Formulas (1), (3), (4), and (23):
(1)
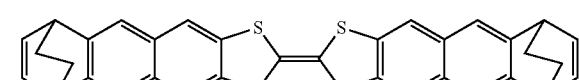
(3)
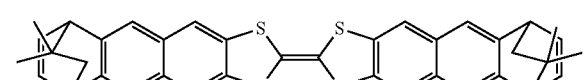
(4)
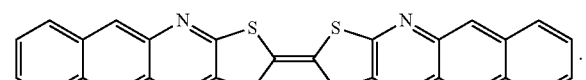
(23)
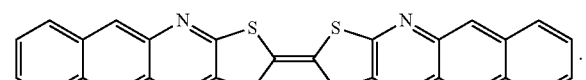
6. A semiconductor, comprising the tetrathiafulvalene derivative of claim 1.
7. The semiconductor of claim 6, wherein the semiconductor is a p-type semiconductor.
* * * * *